(12) United States Patent
Perez-Polo

(10) Patent No.: US 8,399,421 B2
(45) Date of Patent: Mar. 19, 2013

(54) TREATMENT FOR NEUROPATHIC PAIN DUE TO SPINAL CORD INJURY

(75) Inventor: J. Regino Perez-Polo, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 177 days.

(21) Appl. No.: 12/079,956

(22) Filed: Mar. 31, 2008

(65) Prior Publication Data

US 2008/0242634 A1 Oct. 2, 2008

Related U.S. Application Data

(66) Substitute for application No. 60/909,050, filed on Mar. 30, 2007.

(51) Int. Cl.
  *C12N 15/11* (2006.01)

(52) U.S. Cl. .................................... 514/44 A
(58) Field of Classification Search ............... 514/44 A
  See application file for complete search history.

(56) References Cited

U.S. PATENT DOCUMENTS

| 7,408,022 B2 * | 8/2008 | Lin et al. ................. 530/300 |
| 2004/0071711 A1 * | 4/2004 | Bicknell et al. ........... 424/178.1 |
| 2009/0099108 A1 * | 4/2009 | Jones ........................... 514/44 |
| 2009/0203131 A1 * | 8/2009 | Reineke et al. ............ 435/375 |
| 2009/0214630 A1 * | 8/2009 | Strober et al. ............. 424/450 |

FOREIGN PATENT DOCUMENTS

WO  WO 2005/062854 A3 * 7/2005

* cited by examiner

*Primary Examiner* — Brian Whiteman

(57) ABSTRACT

The present invention is drawn to treatment of neuropathic pain due to spinal cord injury. In this regard, the present invention discloses methods and composition to treat neuropathic pain.

7 Claims, 13 Drawing Sheets

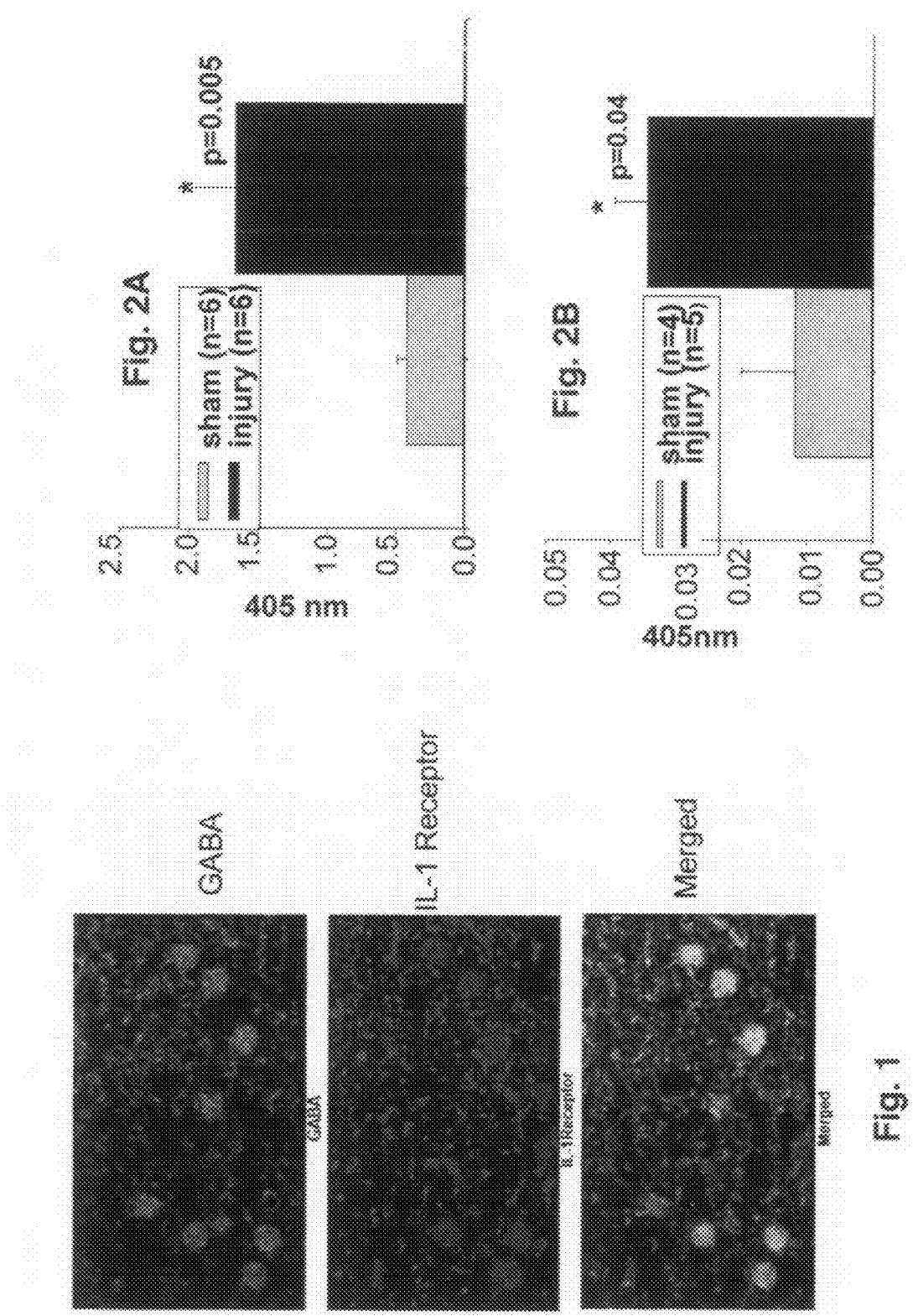

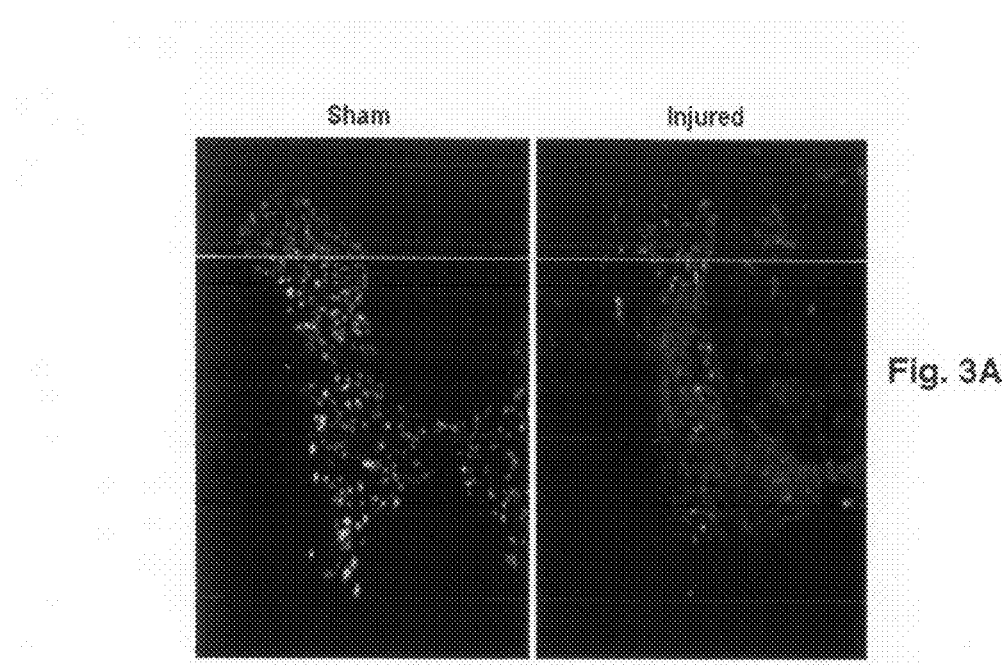
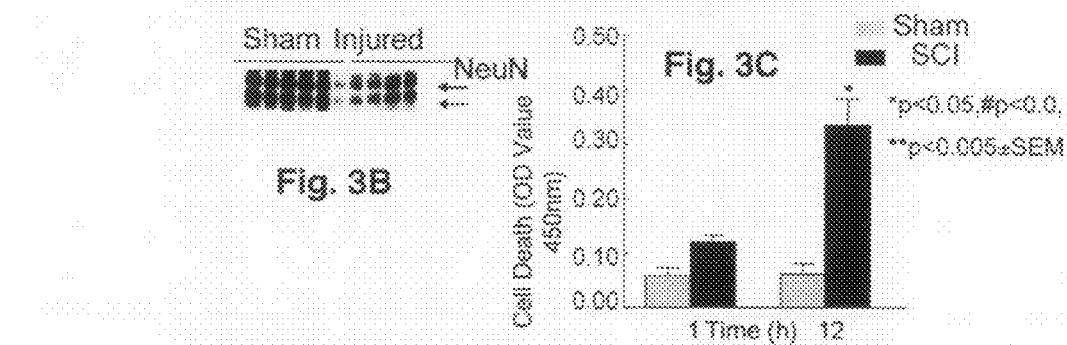
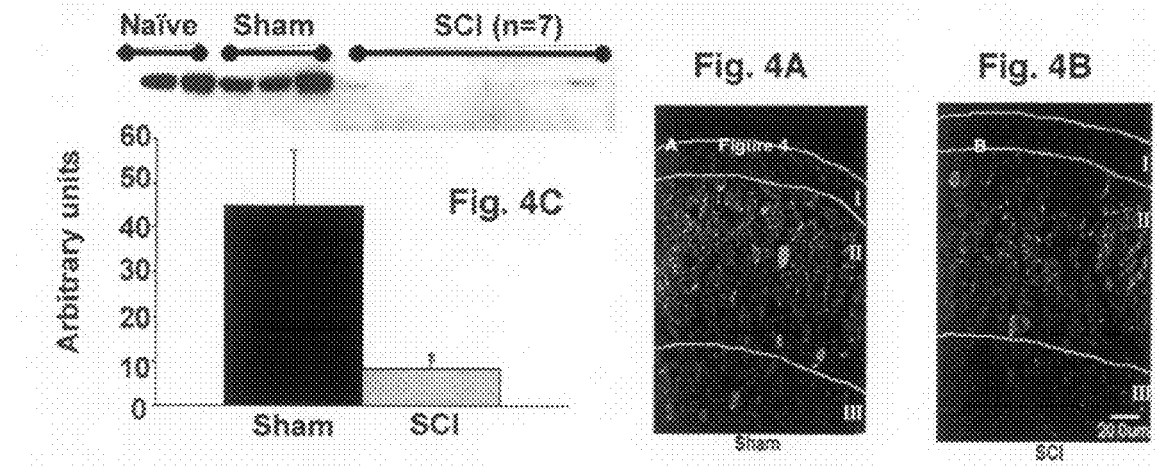

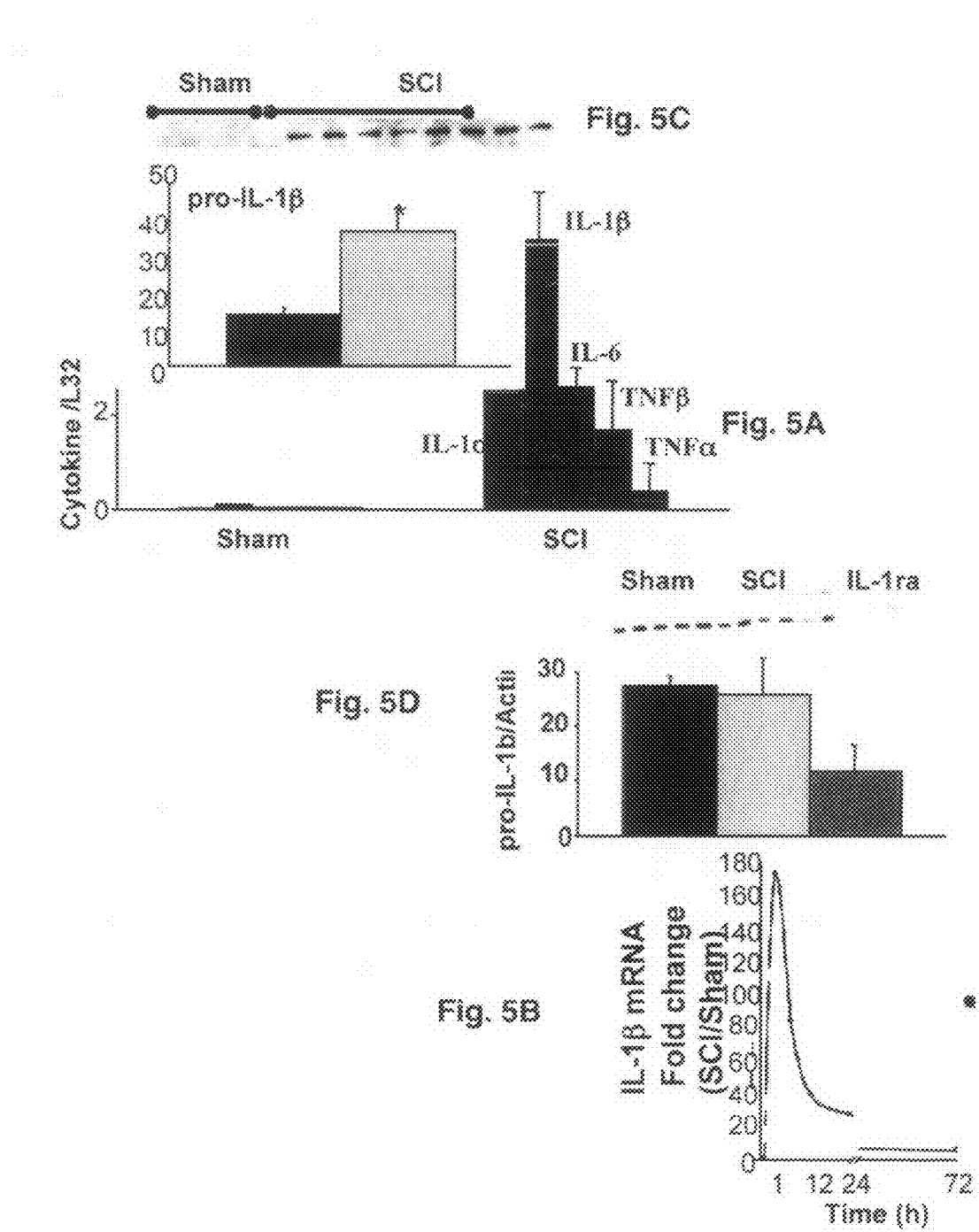

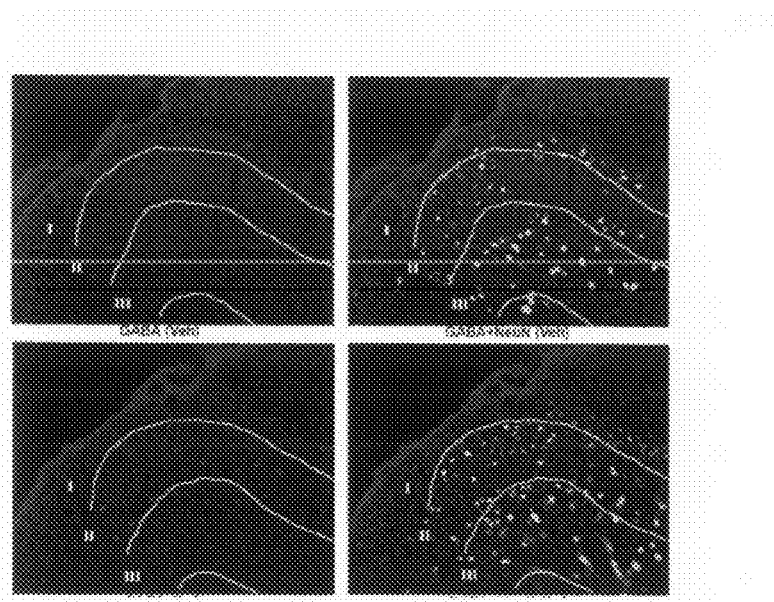
Fig. 6A
Fig. 6B
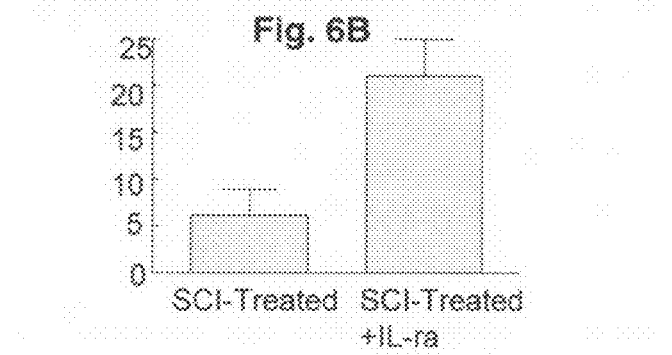
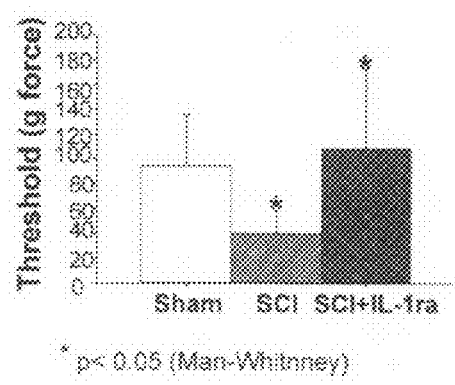
Fig. 7
* p< 0.05 (Man-Whitney)

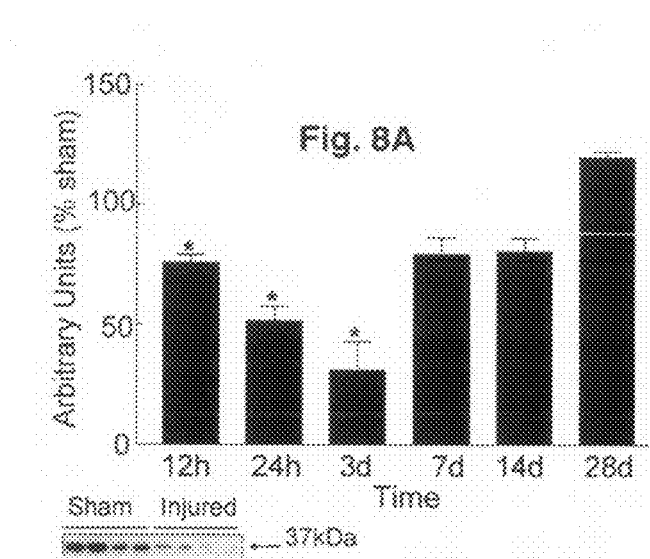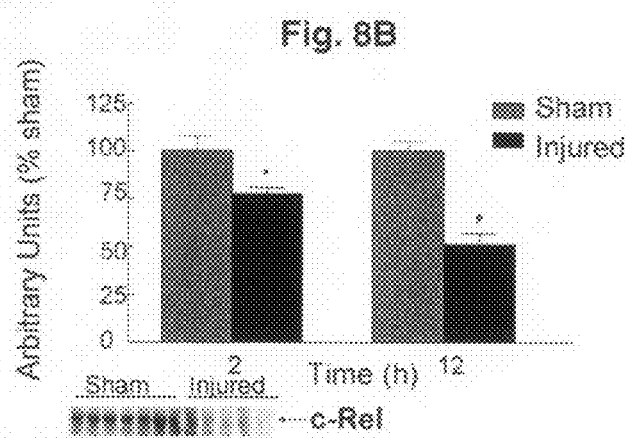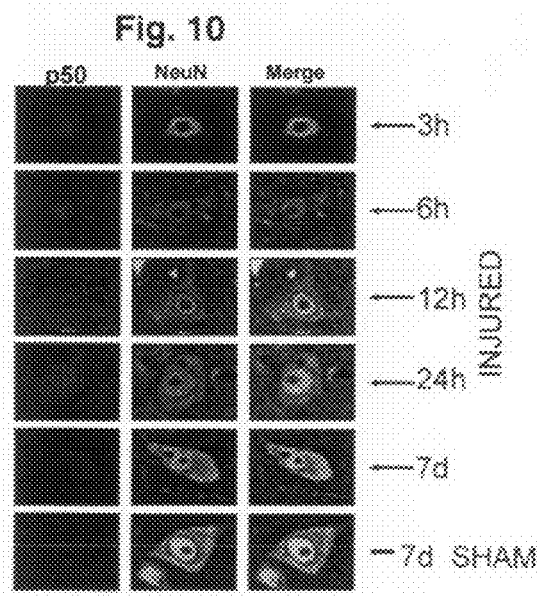

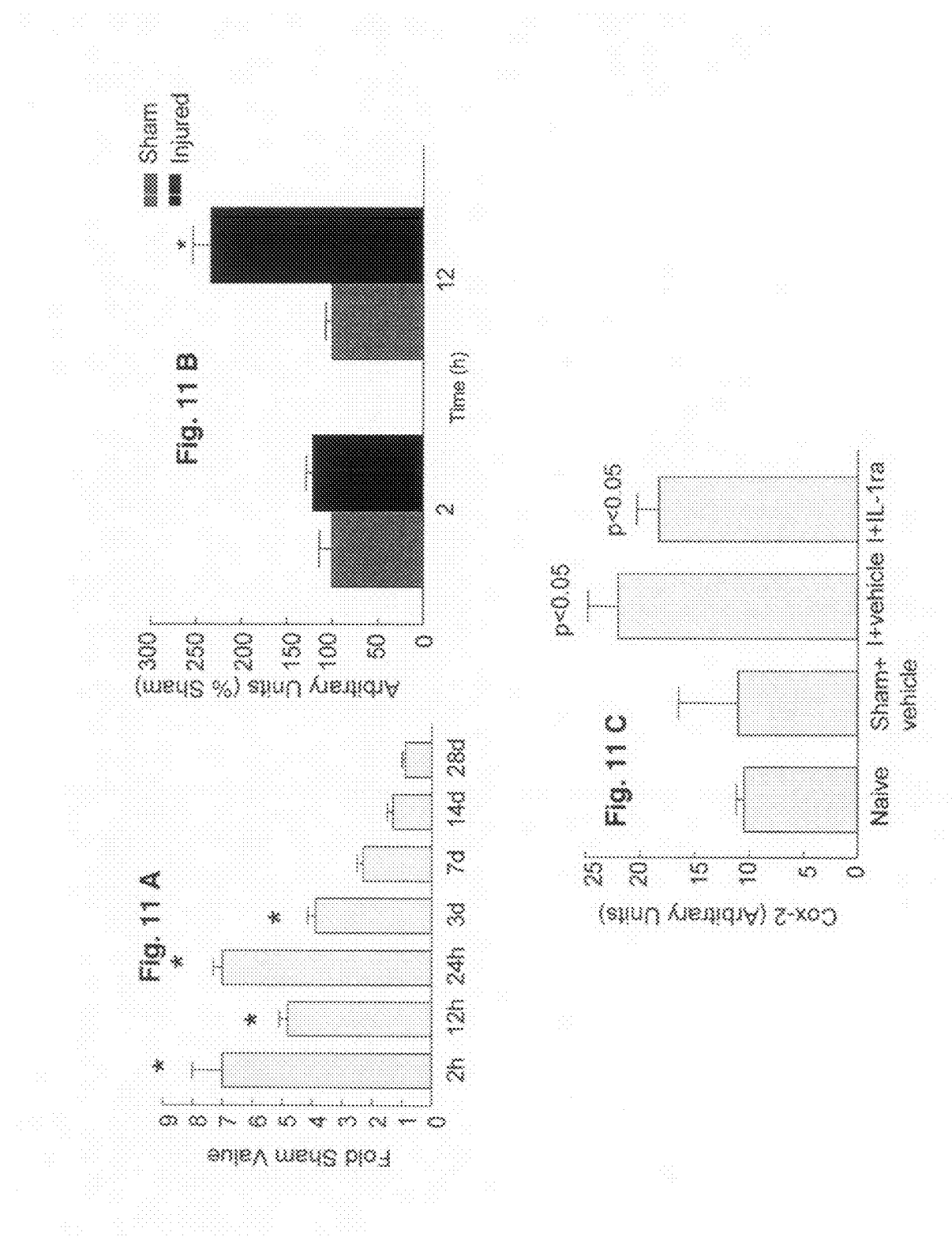

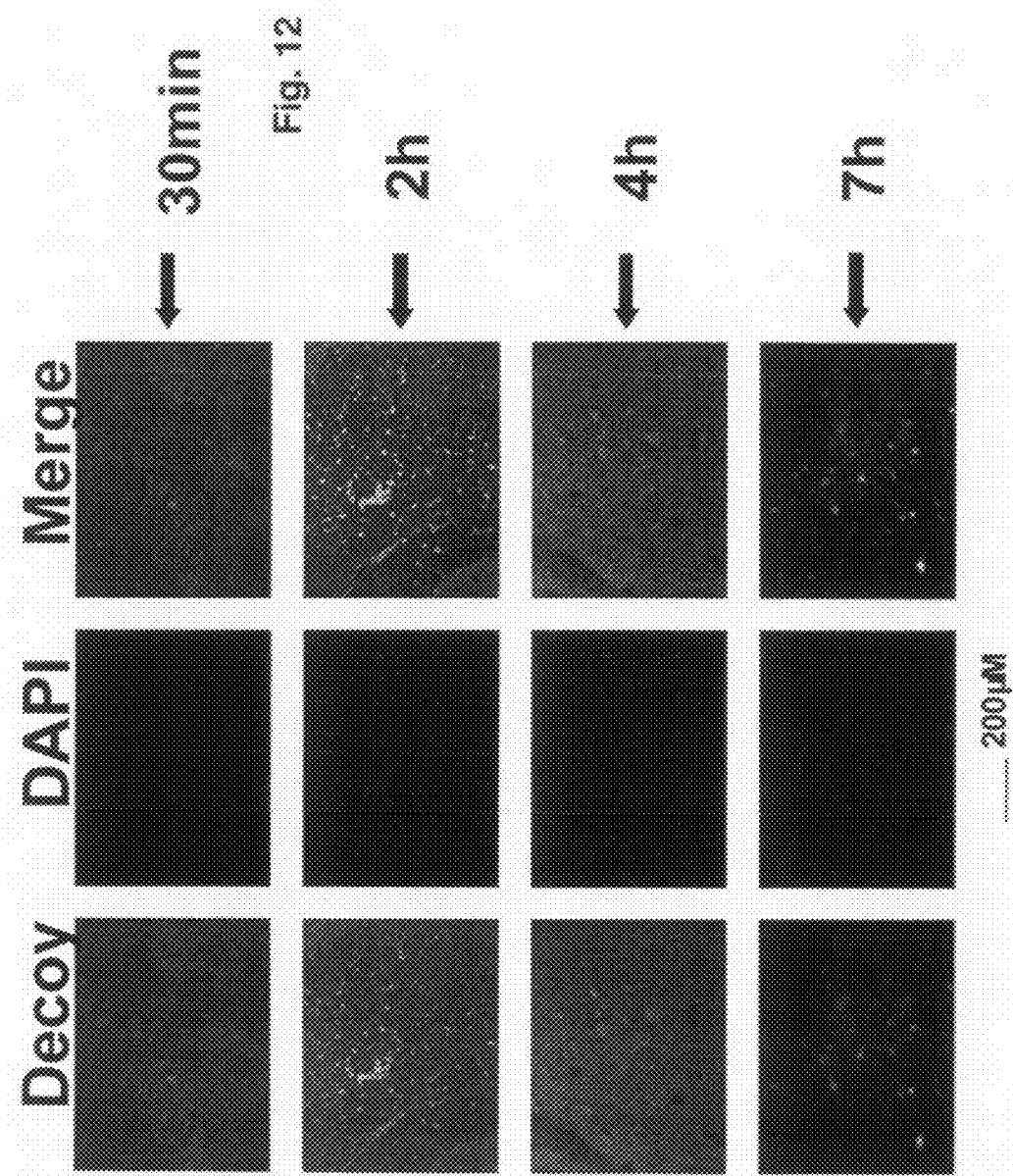

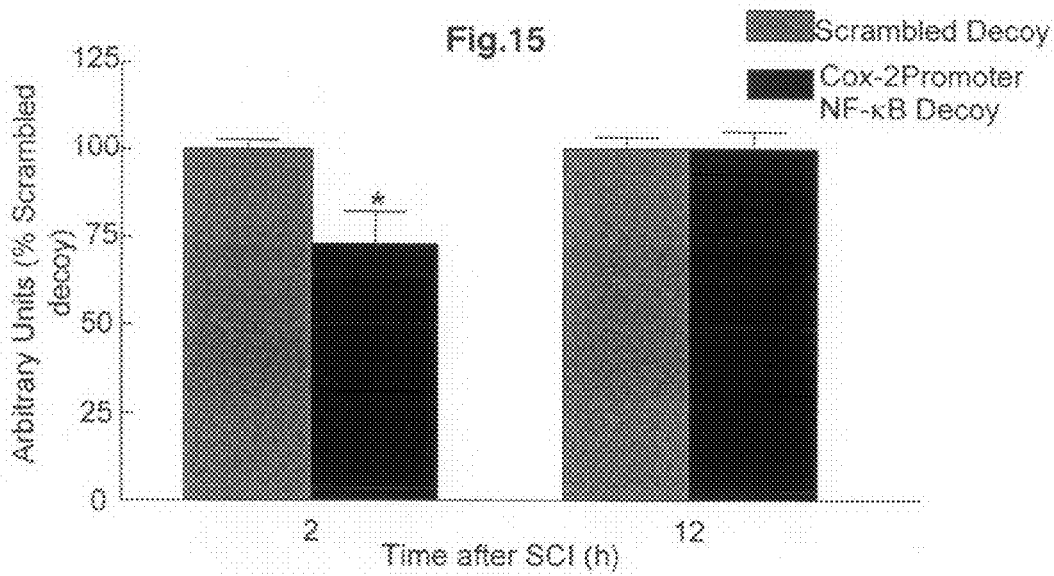
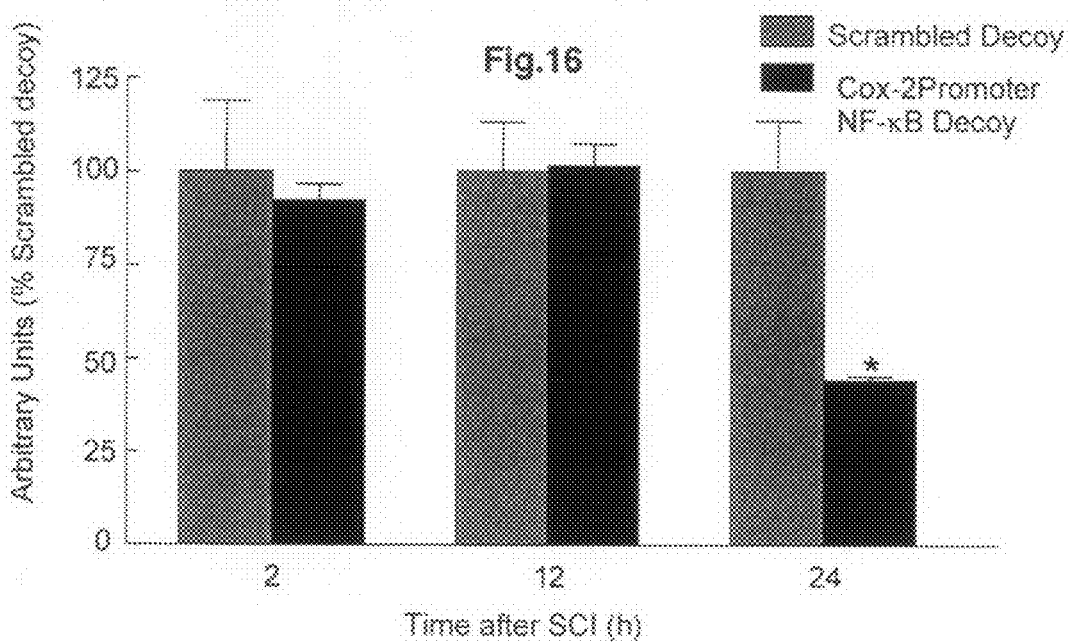

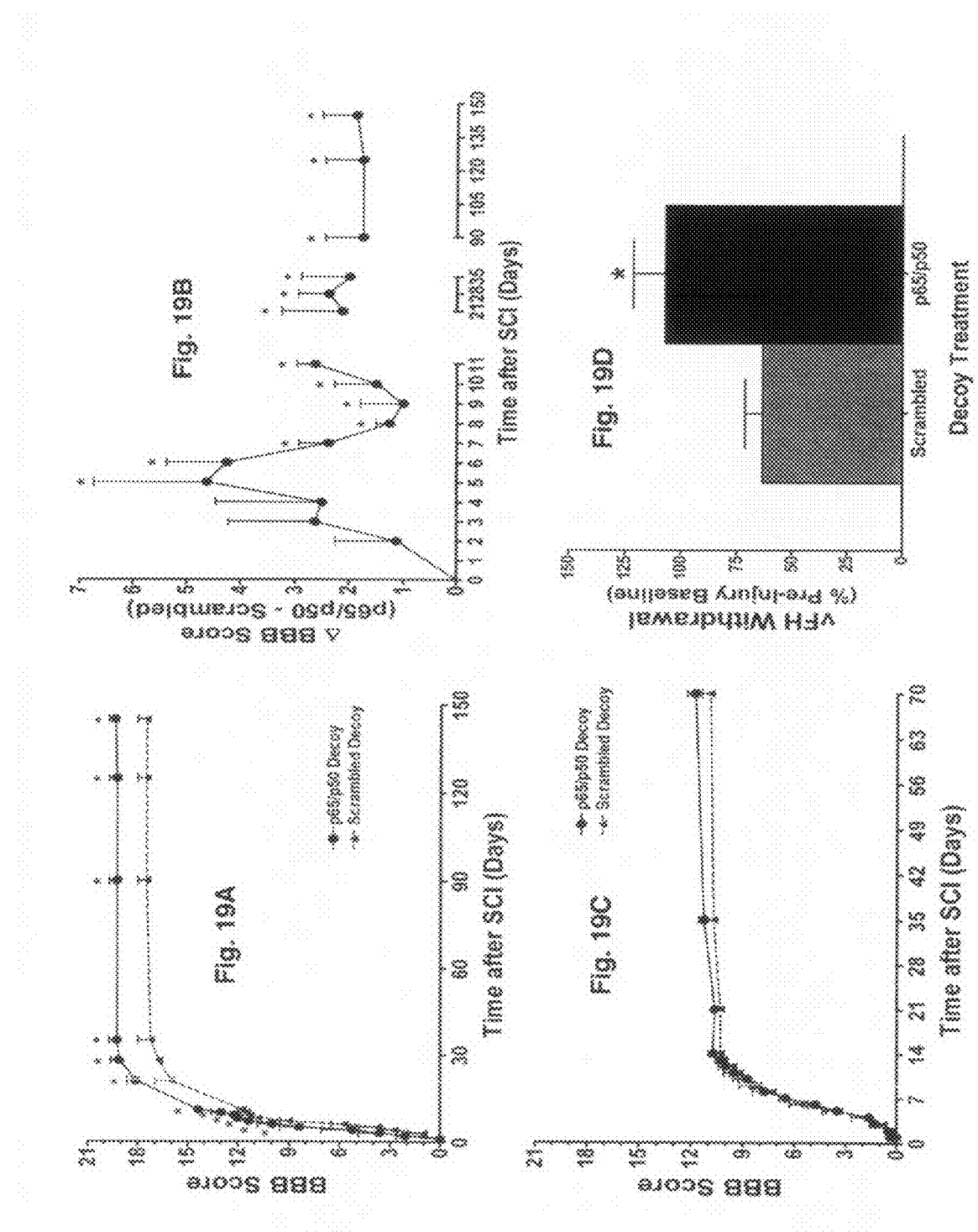

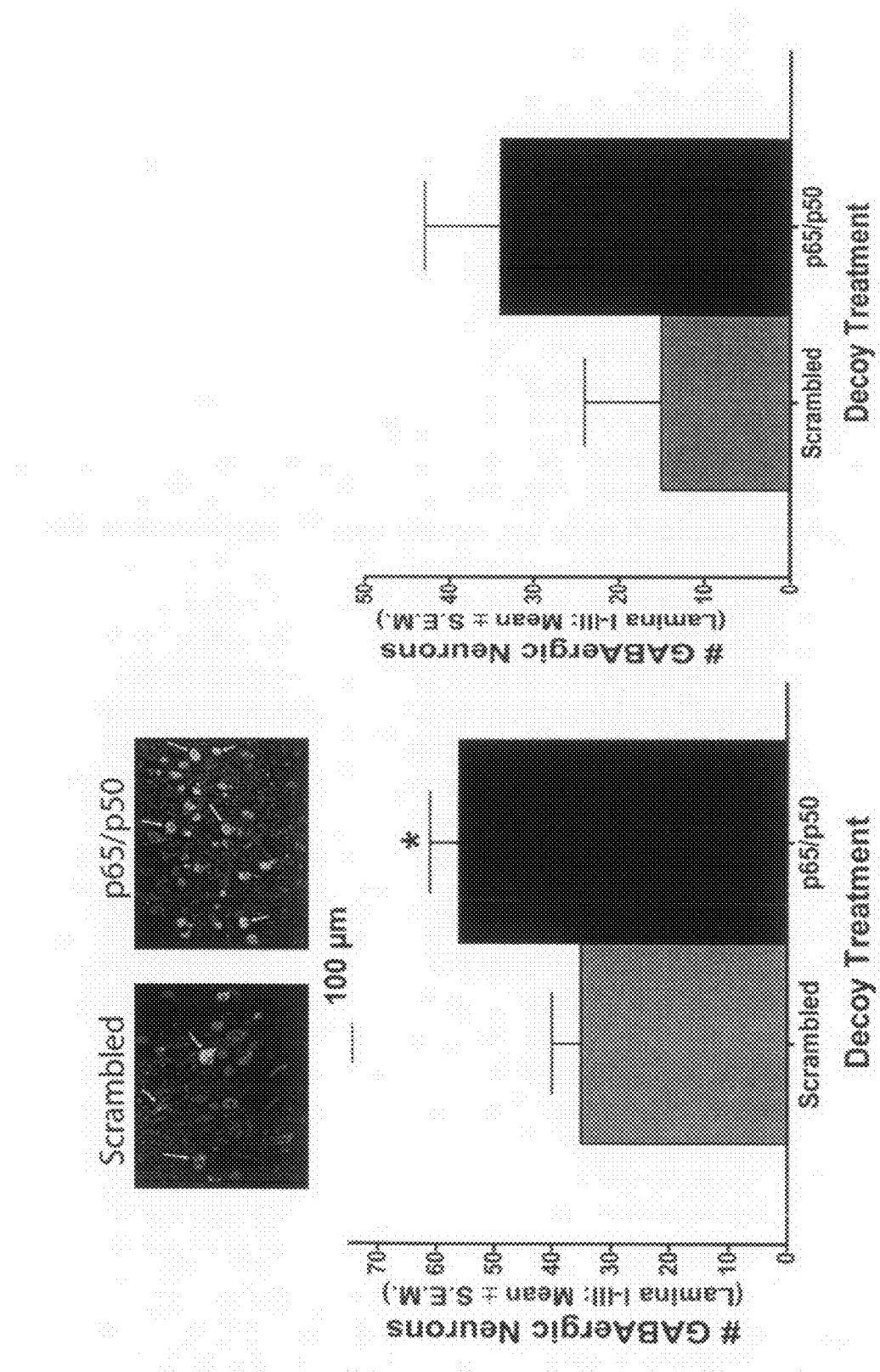

SEQUENCE LISTING

<160> NUMBER OF SEQ ID NOS: 6

<210> SEQ ID NO 1
<211> LENGTH: 20
<212> TYPE: DNA
<213> ORGANISM: artificial sequence
<220> FEATURE:
<223> OTHER INFORMATION: Cox-2 sequence

<400> SEQUENCE: 1
ggcaagggga ttcccttagt                     20

<210> SEQ ID NO 2
<211> LENGTH: 20
<212> TYPE: DNA
<213> ORGANISM: artificial sequence
<220> FEATURE:
<223> OTHER INFORMATION: IgG kappaB sequence

<400> SEQUENCE: 2
ttgaggggac tttcccaggc                     20

<210> SEQ ID NO 3
<211> LENGTH: 20
<212> TYPE: DNA
<213> ORGANISM: artificial sequence
<220> FEATURE:
<223> OTHER INFORMATION: scrambled sequence

<400> SEQUENCE: 3
cgatcatagt atctgcactg                     20

<210> SEQ ID NO 4
<211> LENGTH: 21
<212> TYPE: DNA
<213> ORGANISM: artificial sequence
<220> FEATURE:
<223> OTHER INFORMATION: Bcl XL sequence

<400> SEQUENCE: 4
tttgtggggg gtctccagca t                   21

<210> SEQ ID NO 5
<211> LENGTH: 10
<212> TYPE: DNA
<213> ORGANISM: artificial sequence
<220> FEATURE:
<223> OTHER INFORMATION: IgG kappaB enhancer sequence

<400> SEQUENCE: 5
gggactttcc                                10

<210> SEQ ID NO 6
<211> LENGTH: 10
<212> TYPE: DNA
<213> ORGANISM: artificial sequence

```
<220> FEATURE:
<223> OTHER INFORMATION: Cox-2 promoter sequence

<400> SEQUENCE: 6
ggggattccc                                                                  10
```

TREATMENT FOR NEUROPATHIC PAIN DUE TO SPINAL CORD INJURY

CROSS REFERENCE TO RELATED APPLICATION

This non-provisional application claims benefit of provisional application U.S. Ser. No. 60/909,050 filed on Mar. 30, 2007, now abandoned.

FEDERAL FUNDING LEGEND

This invention was produced using funds obtained through a National Institutes of Health, NINDS grant (N539161). Consequently, the Federal government has certain rights in this invention.

BACKGROUND OF THE INVENTION

1. Field of the Invention

The present invention relates generally to the field of molecular biology, cell signaling pathways and treatment of pain in neurologic diseases. More specifically, the present invention provides method to treat of neuropathic pain, including but not limited to those caused by from spinal cord injury.

2. Description of the Related Art

There are approximately 11,000 spinal cord injuries (SCI) in the United States per year, and over half of all spinal cord injuries patients develop chronic neuropathic pain (CNP). Primary injury to the spinal cord results in neuronal and glial cell death with apoptotic features (Hains et al., 2001; Nesic et al., 2001; Beattie, 2004; DeNovellis et al., 2004; Tachibana et al., 2005).

GABA is an inhibitory transmitter in the spinal cord found in a large fraction of the interneurons within the dorsal horn. These neurons are inhibitory on dorsal horn neurons that are part of somatosensory circuits included in pain (Willis and Coggeshall, 1991). Intraspinal GABAergic terminals from interneurons, which are presypnaptic to central terminals of nocicieptive primary afferents, release GABA, generating primary afferent depolarization (Granados-Soto et al., 2005). There are several reports that support the hypothesis that GABAergic deficits can result in the activation of nociceptive pathways after spinal cord injury (Jasmin et al., 2004; Weng and Dougherty, 2005). deNovellis et al., (2004) showed that glutamate receptor blockade in a sciatic nerve injury model of neuropathic pain correlated with decreased lamina II cell death and injury-induced Bax increases as well as allodynia. In the ischemic model of SCI developed in Wiesenfeld-Hallin's laboratory, there is a loss of GABAergic neurons (Zhang et al., 1993). The loss of GABA expression corresponds temporally with the onset of acute mechanical allodynia, which develops within 4 to 8 hrs, lasts several days, and is blocked by systemic administration of both NMDA and non-NMDA antagonists and the $GABA_B$ agonist, baclofen (Xu, et. al., 1992).

Baclofen, an agonist of the gamma-aminobutyric acid (GABA) receptor, has anti-nociceptive effects, and its intrathecal administration reduces allodynic responses in animal models of neurogenic central pain. In a clinical trial it was found that baclofen diminished spontaneous and evoked (allodynia) dysesthetic pain among patients with spinal injury (Herman et al., 1992; Taira et al., 1995). Evidence that GABA plays a major role in the central hyperexcitabilty associated with nerve damage is that systemic administration of blood-brain barrier-permeant GABA(A) receptor agonists attenuates nociceptive behaviours in a sciatic nerve ligation model of peripheral neuropathic pain (Rode et al., 2005), while blockade of spinal GABA(A) receptors leads to mechanical allodynia in rats (Heinke et al., 2004). Four weeks after spared nerve injury, the cumulative loss of dorsal horn neurons, determined by stereological analysis, is >20% (Coggeshall et al., 2001). GABAergic inhibitory interneurons are among the neurons lost, and a marked decrease in inhibitory postsynaptic currents of lamina II neurons coincides with the induction of apoptosis. Blocking apoptosis with the caspase inhibitor benzyloxycarbonyl-Val-Ala-Asp(OMe)-fluoromethylketone (ZVAD) prevents the loss of GABAergic interneurons in lamina II, and decreases inhibitory currents and pain hypersensitivity (Coggeshall et al., 2001; Scholz et al., 2005). Thus, one source of decreased GAD after injury could be cell death of GABAergic neurons, albeit the model used was not contusion SCI but damage to sciatic nerve (Moore et al., 2002). It is not that simple because GABAergic neurones in spinal lamina II are not homogenous in terms of their expression of glycine, parvalbumin and nNOS (Heinke et al., 2004).

Cyclooxygenase-2 is the rate limiting enzyme for the conversion of arachidonic acid into prostaglandins. Normally COX-2 is localized in the soma and dendrites of glutamatergic neurons (Kaufmann, et al, 1996) and induced by synaptic activity (Yamagata, et al, 1993). However, increases in the inducible form, COX-2, during spinal cord injuries are closely related to inflammation. Selective inhibition of COX-2 results in improved functional outcomes following SCI (Resnick, et al, 1998; Hains et al., 2001) and visible decreases in lesion volume and extent (Hains, et al, 2001). IL-1β transcriptional control of COX-2 by NF-κB has been shown in vitro (Newton, et al, 1997), but there is little known about such control mechanisms in vivo in the nervous system.

COX-2 (prostaglandin H2 synthase), the predominant isoform of COX in CNS, produces prostaglandins. SC58125 and S-398 are two common COX-2 inhibitors. Prostaglandin E2 (PGE2) is a product of the cyclooxygenation of arachidonic acid released from membrane phospholipids, plays a critical role in inflammatory neurodegenerative conditions. While the use of COX-2 inhibitors is useful in mechanistic studies of CNS trauma (Hains et al., 2001), their adverse side effects do not make them promising therapeutic agents (Turini and Dubois, 2002; Flower, 2003; Topol, 2005). IL-1β-induced COX-2 expression is mediated through NF-kB, p42/p44, and p38 mitogen-activated protein (MAP) kinase in vitro and muscle (Fiebich et al., 2000; Yang et al., 2002). The human COX-2 gene contains NF-kB binding sequences. Use of various inhibitors showed that IL-1β stimulation of NF-kB increases COX-2. There is an early transient and robust post-SCI increase in IL-1β levels (Wang, et al, 1997), which has been shown to contribute significantly to augmentation of COX-2 (Tonai, et al, 1999), which stimulates production of reactive oxygen species ($O_2$—, OH—, NO—), in part via COX-2 and iNOS activity. IL-1β stimulates nuclear factor-kappa B (NF-κB) activation, a transcription factor known to regulate COX-2 and iNOS (Newton, et al, 1997). iNOS binds COX-2 and S-nitrosylates it, enhancing COX-2 catalytic activity.

NF-κB/Rel family: The transcription factor "NF-κB" consists of homo- or hetero-dimers of subunits which constitute a family of related proteins, including p50, p52 (also called p49), p65 (also called RelA), c-Rel and RelB. All of them contain a highly conserved ~300 residue $NH_2$-terminal domain for DNA binding/dimerization (Rel homology domain), which enables them to form dimers and bind to an array of homologous decanucleotide sequences with varying affinities. NF-κB/Rel proteins can be divided into two classes based on their c-terminal domain. One class includes p65, c-Rel and RelB proteins, which contain a c-terminal transactivation domain. The other class includes p50 and p52, which have no transactivation domain at c-terminus. The most commonly described active NF-κB subunit combinations are the p65/p50 and c-rel/p50 heterodimer. Homodimeric combinations of p50 or p52 have no transactivation activity and often behave in vivo as transcriptional inhibitors (Franzoso et. al., 1992; 1993a).

NF-κB is expressed constitutively in neurons (Kaltschmidt et al., 1994) and activated in the forebrain and hippocampus following hypoxia/ischemia (Koong, et al., 1994; Schmidt, et al., 1995; Yang et al. 1995, Qiu et al., 2001) and; cortex after traumatic brain injury (Yang, et al., 1995). The transcription factor NF-κB is reported to regulate cell death by modulating a diverse array of genes which are important for both cell death and survival, such as Bcl-2, Bcl-$x_L$, MnSOD, iNOS, COX-2, and some pro-inflammatory cytokines (IL-1α/β, TNF-α/β) (Foster-Barber et al., 2001; Lau and Yu, 2001; Saliba and Henrot, 2001). The extent to which NF-κB activation contributes to neuropathology vs. neuroprotection and recovery remains unresolved. In a number of experimental models, including cell lines and tissues under different stimuli, NF-κB activation appears to result in both apoptotic and anti-apoptotic outcomes (Abbadie et al., 1993). For example, the p65/p50 dimer may activate genes coding for proteins with pro-apoptotic properties, while c-Rel/p50 dimer may activate genes coding for proteins that prevent cell death (Qiu et al., 2001). Therefore, different stimuli might activate different NF-κB dimers, resulting in beneficial or detrimental outcomes. Although the activation of p65/p50 dimers after spinal cord injuries has been a subject of study, less is known about the role of c-Rel/p50 dimers in spinal cord injuries.

Movement of NF-κB proteins into the nucleus and binding to DNA is controlled by a family of negative regulators, the IκB family (IκBα, IκBβ, IκBγ and Bcl-3; Haskill, et. al., 1991; Thompson, et. al., 1995). IκBα binds NF-κB dimers preventing nuclear translocation. In response to stimuli that include IL-1 and TNF-ζ, IκB is phosphorylated, ubiquitinated and degraded, exposing nuclear localization signals on NF-κB proteins to allow nuclear translocation. Interestingly, only the NF-κB dimers that contain at least one trans-activation members (p65, c-Rel or Rel-B) are effectively regulated by IκBα.

Despite this, prior art is deficient in method to treat neuropathic pain, including those caused by spinal cord injury. The current invention fulfils this long standing need in the art.

SUMMARY OF THE INVENTION

In one embodiment of the present invention, there is provided a method for treating neuropathic pain in an individual. Such a method comprises the step of administering pharmacologically effective amounts of a IL-1 receptor antagonist (IL-1ra) to the individual, thereby treating the neuropathic pain in the individual.

In a related embodiment of the present invention, there is provided a method for treating neuropathic pain in an individual. Such a method comprises administering a compound that alters inflammatory cascade at the NF-κB level in the individual, thereby treating neuropathic pain in the individual. In another related embodiment of the present invention, there is provided a method for altering the inflammatory cascade in spinal cord injury. Such a method comprises modulating the inflammatory cascade at the IL-1 receptor level, downstream thereof at the NF-κB level or both.

BRIEF DESCRIPTION OF THE DRAWINGS

The appended drawings have been included herein so that the above-recited features, advantages and objects of the invention will become clear and can be understood in detail. These drawings form a part of the specification. it is to be noted, however, that the appended drawings illustrate preferred embodiments of the invention and should not be considered to limit the scope of the invention.

FIG. 1 shows immunocytochemical staining of cells in laminae II. The staining shows GABA (red) and IL-1R (green) in the same cells (yellow) in laminae II of segment T8, 24 h after SCI.

FIGS. 2A-2B show apoptosis evaluations performed at T8, 3 days after SCI. FIG. 2A shows apoptosis evaluations performed using the presence of cytoplasmic histone-DNA complexes and FIG. 2B shows caspase-3 activity measured as cleavage of substrate consisting of tetrapeptide (DEVD) and a chromogen.

FIGS. 3A-3C show apoptosis evaluations after spinal cord injuries. In FIG. 3A, sham and injured spinal cords were compared for staining of the neuronal specific marker, NeuN (green) at T8. The lack of punctate staining in the spinal cord at the injury site demonstrates the loss of neurons in gray matter (100×). FIG. 3B shows representative western blot used to analyze nuclear NeuN protein levels at level (black) vs sham-treated (gray) after 2, 12 and 24 h. (Sham: n=4, Injured: n=5). In FIG. 3C, the values are means±SEM normalized to shams. *$p<0.05$, #$p<0.01$, **$p<0.005$ vs sham treated (two-tailed Student's t-test).

FIG. 4A-4C show effects of spinal cord injuries on GABA labeling in lamina I-III, 24 h after SCI at T8. FIG. 4A shows sham-treated and FIG. 4B shows SCI-treated. FIG. 4C shows western blot assay for GAD67 comparing naïve (n=2), sham treated (n=3) and SCI-treated (n=7; $p<0.01$ vs sham).

FIGS. 5A-5D show effect of IL-1 after spinal cord injury. In FIG. 5A, cytokine mRNA levels at T8 were measured by RPA (*$p<0.05$; Nesic et al., 2002). FIG. 5B shows IL-1β mRNA measured 1, 6, 24 and 72 hrs after spinal cord injury. FIG. 5C shows pro-IL-1β measured by Western blots 4 hrs after spinal cord injury. A robust increase in IL-1β at 4 h declines to basal levels 7 days after spinal cord injury. FIG. 5D shows that IL-1ra (14.3 mg/ml, osmotic minipump, 1 ul/h) administered for 7 days significantly decreased basal IL-1β levels.

FIGS. 6A-6B show a significant increase in the number of spared GABAergic neurons in laminae I-III from contused rats treated with IL-1ra. FIG. 6A shows imaging of GABA (red) and NeuN (green) and merged stains (yellow) in dorsal horn at T8 of rat cords contused at T10 at 3d. Upper panel is SCI, lower panel is SCI-IL-1ra treated. FIG. 6B shows cells counts to demonstrate increased sparing of GABAergic neurons by IL-1ra treatment. P<0.05 per section.

FIG. 7 shows ameliorative effect of IL-1ra treatment on a _-level allodynia (girdling).

FIGS. 8A-8B shows results of western blot analysis for evaluating the consequence of IL-1ra blockade on spinal cord injury-induced NF-κB activation of COX-2 transcription. FIG. 8A shows cytoplasmic levels of IκB-α and FIG. 8B shows cytoplasmic levels of nuclear c-Rel after spinal cord injury at T8 (n=4 per group). Values are means±SEM, and are normalized to the sham group (not shown). *$p<0.05$, #$p<0.01$ vs sham treated group (two tailed Student's t-test). Representative blots shown.

FIG. 10 shows co-localization of p50 (red) immunoreactivity with neuron specific marker, NeuN (green), indicated by yellow in the merged panel. These representative photomicrographs show increased neuronal p50 protein expression up to 24 h after SCI at T8. Sham photomicrographs from 7d animals are representative of all corresponding time points tested (100×).

FIGS. 11A-11C changes in Cox-2 protein levels after SCI in injured rats by western blot analysis. FIG. 11A shows COX-2 levels at T8 with time after SCI. Values are means±SEM normalized to shams. *p<0.05 vs sham-treated (two-tailed Student's t-test). Representative blot shown. FIG. 11B shows iNOS levels after SCI (black) and sham-treated (gray) at 2 and 12 h (sham n=4, SCI n=5). *p<0.001 vs sham-treated group (two-tailed Student's t-test). FIG. 11C shows COX-2 protein levels at T8, 24 h after treating SCI rats with IL-1ra.

FIG. 12 shows distribution of decoy deoxyoligonucleotides after injection into injured spinal cord. Fluorescein-labeled decoys (green) disperse throughout the site on injury (T10). Co-localization with nuclear marker, DAPI (blue) is observed at 2 h. Maximal decoy dispersion and penetration occurred 2 and 4 hrs after treatment (100×).

FIG. 15 shows effect of Cox-2 promoter NF-κB decoy on Cox-2 protein expression after SCI. Western blots were used to analyze the injury site for cytoplasmic levels of Cox-2 protein in Cox-2 decoy (black bars) and scrambled decoy treated SCI rats (gray bars) at 2 and 12 h (n=4 for 2 h group, n=5 for 12 h group). Values are means±SEM and are normalized to sham group (not shown). *p<0.05 compared to age-matched sham-treated group (two-tailed Student's t-test). Representative blot is shown.

FIG. 16 shows effects of Cox-2 promoter NF-κB decoy on iNOS protein expression after spinal cord injury. Western blots were used to analyze the injury site for cytoplasmic levels of iNOS protein in Cox-2 decoy (black bars) and scrambled decoy treated rats (gray bars) at 2, 12 and 24 h (n=4 for 2 h, n=5 for 12 h, n=6 for 24 h). Values are ±SEM normalized to sham group (not shown). *p<0.05 compared to age-matched sham-treated group (two-tailed Student's t-test). Representative blot is shown.

FIGS. 19A-19D show effects of Cox-2 promoter NF-κB decoy on clinically relevant outcomes. FIG. 19A shows locomoter recovery after 150-kDyne SCI in Cox-2 promoter NF-κB decoy-treated rats. BBB scores were measured in Cox-2 promoter NF-κB decoy (solid line)- and scrambled decoy (dashed line)-treated rats over a 145 day period (Cox-2 promoter NF-κB decoy: n=5, scrambled: n=3). All animals injured at T10. FIG. 19B shows daily difference in BBB scores between Cox-2 promoter NF-κB decoy- and scrambled decoy-treated groups. Values are mean±SEM. *p<0.025. All animals injured at T10. FIG. 19C shows locomoter recovery after 200-kDyne SCI in Cox-2 promoter NF-κB decoy-treated rats. BBB scores were measured in Cox-2 promoter NF-κB decoy (solid line)—and scrambled decoy (dashed line)—treated rats over a 70-day period (Cox-2 promoter NF-κB decoy: n=9, scrambled: n=11). There is no significant difference in locomoter scores observed. Values are mean±SEM. All animals were injured at T10. FIG. 19D shows effects of Cox-2 promoter NF-κB decoys on mechanical sensitization after SCI. The modified Dixon up-down method was employed to test sensitivity to mechanical forces in SCI rats injected with Cox-2 promoter NF-κB decoy (blac bars) and scrambled decoy (gray bars). Measurements were taken before injury and 10 weeks after SCI and treatment (Cox-2 promoter NF-κB decoy: n=9, scrambled: n=11). Each group is represented as a percentage of preinjury measurements. Values are mean±SEM. *p<0.02. All animals injured at T10.

FIGS. 20A-20B show effect of Cox-2 promoter NF-κB decoy treatment after SCI on hypersensitivity. FIG. 20A shows effects of Cox-2 promoter NF-κB decoy-treatment on GABAergic neuronal populations after SCI. Representative photomicrographs of spinal cord ventral horn laminae 1-3 from rostral sections (T9) showing colocalization of GABA (red) immunoreactivity with neuronal specific marker NeuN (green) and DAPI (blue) as indicated by white arrows. X400.

Significantly more GABAergic neurons were seen in the Cox-2 promoter NF-κB decoy-treated group compared to the scrambled treated group (graph). *p<0.02. All animals were injured at T10. FIG. 20B shows representative photomicrographs of spinal cord ventral horn laminae 1-3 from the cervical enlargement (C7/C8) showing colocalization of GABA 9red) immunoreactivity with neuronal specific marker NeuN (green) and DAPI (blue), as indicated by the yellow color in the merged panel. Injury occurred at T10. Sham photomicrographs from 7-day animals are representative of all corresponding time points tested. All animals were injured at T10. X400.

DETAILED DESCRIPTION OF THE INVENTION

Figure 9:
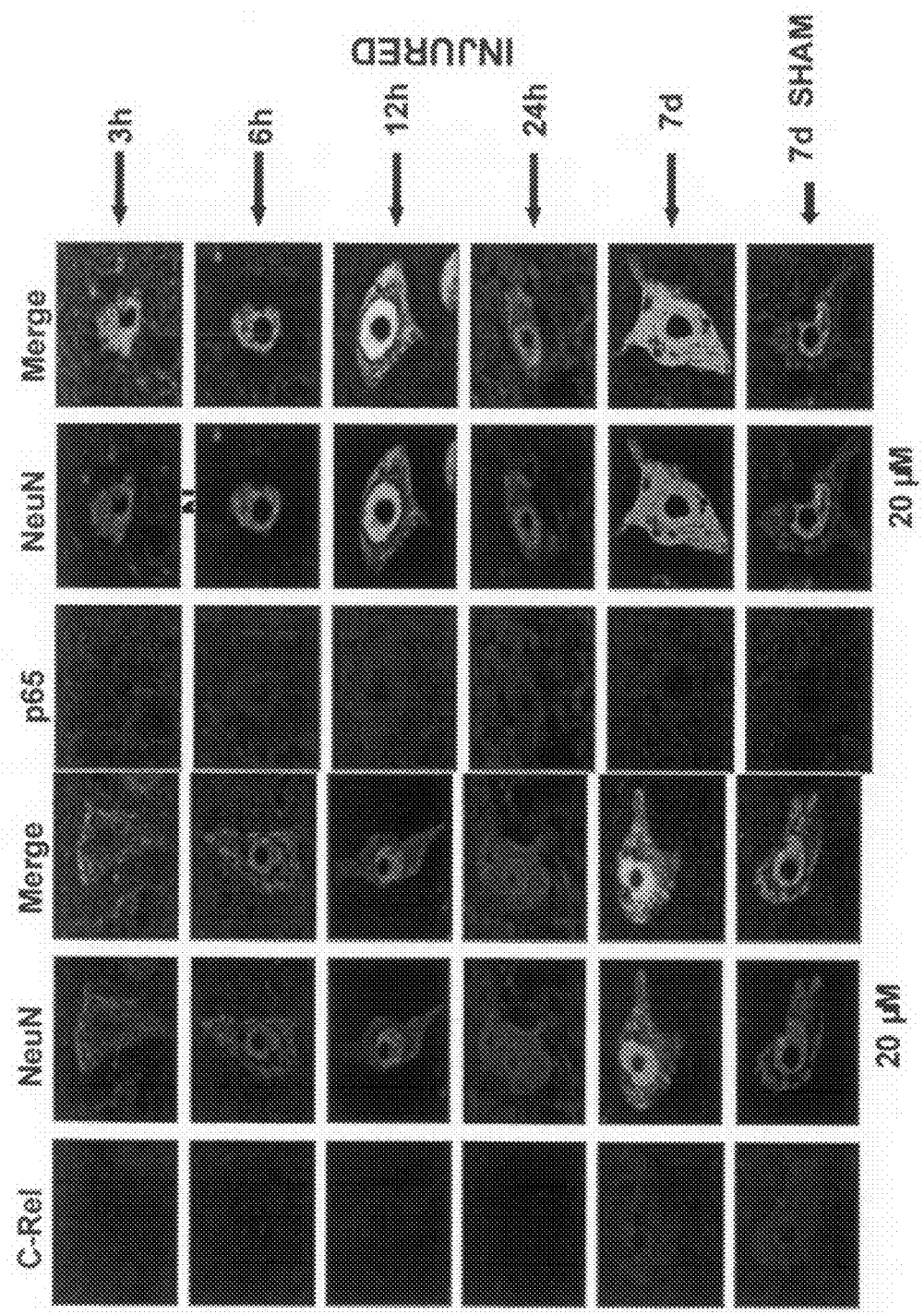
FIG. 9 shows consequence of IL-1ra blockade on expression pattern of NF-κB proteins using confocal microscopy. Comparison of c-Rel (red) and neuronal marker NeuN (green) immunoreactivity. Co-localization is yellow in the merged panel. These photomicrographs show decreased neuronal c-Rel protein expression up to 24 h after spinal cord injury. (Right) comparison of p65 (red) with NeuN (green) immunoreactivity. Co-localization is yellow. These photomicrographs show increased neuronal p65 protein expression at T8 up to 24 h after SCI. Photomicrographs from sham-treated 7d animals are representative of all shams at all times (1000×).

The present invention is drawn to the treatment of neuropathic pain due to spinal cord injury. Briefly, the present invention discloses that there is significant GABAergic loss associated with contusion spinal cord injury, in terms of both cell loss and decreased GAD enzyme. The present invention also demonstrates apoptotic features shown by neurons in injured segments. More importantly, the present invention discloses that GABAergic neurons of lamina I-III display IL-1R.

Further, there was a 40% increase in the number of NeuN$^+$ cells in IL-1ra-treated rat cords after spinal cord injury. Additionally, there was a significant improvement (14%) in BBB scores (assessment of locomoter function) and decreased SCI induction of COX-2 in the IL-1ra-treated rats. More importantly, IL-1ra had an interesting effect on girdling in SCI-treated animals at 35 days. The SCI-treated group had significantly lower threshold compared to the sham group (*p<0.05) and to the presurgical data, while the IL-1ra-treated groups showed a statistically significant threshold increase compared to vehicle-treated SCI (p<0.05). In other words, IL-1ra treatment returned the mechanical allodynia in the trunk region at the level of the lesion to the values that were not statistically significantly different from sham values. Thus, the results presented herein show that blocking the inflammatory cascade at IL-R level can decrease the neuronal cell loss, allodynia and also improve locomoter function.

Furthermore, the present invention discloses that IL-1ra or Cox-2 promoter NF-κB decoys can be used in the treatment of neuropathic pain due to spinal cord injury. Although the underlying mechanisms of cell death and dysfunction after spinal cord injury are not fully understood, it is known that spinal cord injury stimulates NF-κB activity via inflammatory cytokines (Bethea et al., 1998). The expression profiles of NF-κB subunits after spinal cord injury were characterized and it was observed that c-Rel, an antiapoptotic gene activator (Qiu et al., 2001; Pizzi et al., 2002) decreased in neurons, consistent with the failure of antiapoptotic responses after spinal cord injury. In contrast, NF-κB p65, known to promote inflammatory gene expression, increased in neurons for up to 24 hr after spinal cord injury. The increases in nuclear p65 peaked at 6 hr after injury and return to basal levels by 24 hr are consistent with the negative feedback regulation of p65 via IκB.

NF-κB p50 forms dimers with p65 that stimulate transcription of genes that contribute to inflammation and cell death. The converse is true when p50 forms dimers with c-Rel to promote antiinflammatory gene expression (Van Antwerp et al., 1996). Increases in p50 began early after SCI, as they did for p65, but persisted for 24 hr. This is perhaps a reflection of a sequential increase in inflammatory p65/p50 activity followed by a delayed return to homeostasis by p50/p50 dimer binding alone, without promoter activation, and representing a negative feedback mechanism for transient NF-κB activity increases. There were no detectable changes in NF-κB activity in oligodendroglia after SCI. Thus, NF-κB does not appear to play a role in the death of oligodendroglia after SCI. The immunohistochemical findings are summarized in Table I.

TABLE 1

Immunohistochemical assessment of NF-κB changes after SCI

| | 3 Hr | 6 Hr | 12 Hr | 24 Hr | 7 days |
|---|---|---|---|---|---|
| c-Rel | ↓ | ↓ | ↓ | ↓ | No change |
| p65 | ↑ | ↑ | ↑ | ↑ | No change |
| p50 | ↑ | ↑ | ↑ | | No change |
| p52 | No change | No change | No change | No change | No change |
| RelB | No change | No change | No change | No change | No change |

It was hypothesized that p65/p50-dependent gene transcription was a part of the inflammatory cascade responsible for delayed neuronal death after SCI. The activity of c-Rel, thought to counteract cell death by promoting transcription of cell survival genes, decreased in a more robust fashion than the observed p65 increases, in keeping with there being a preponderance of p65/p50-dependent genes compared with c-Rel/p50-dependent genes.

COX-2 and iNOS are NF-κB p65/p50 targeted genes that promote oxidative stress, subsequent cellular malfunction, cytotoxicity, and eventual cell death. Thus, both COX-2 and iNOS are implicated in the pathogenesis of SCI via their ability to increase reactive oxygen species (ROS) and reactive nitrogen species (RNS), which are potent mediators of cell death in SCI (Braughler and Hall, 1989; Dawson and Dawson, 1996). Inhibition of COX-2 activity has been shown to improve functional outcomes and decrease lesion volume after SCI (Resnick et al., 1998; Hains et al., 2001). Early and long-lasting increases in COX-2 mRNA from 1 to 24 hr after SCI were observed herein. Within the first 24 hr, COX-2 protein expression increased sevenfold, reflecting the increased availability of COX-2 to induce ROS formation and subsequent cell dysfunction and death. There were also delayed and attenuated COX-2 increases in adjacent rostral and caudal segments, a representation of the spreading pathophysiology that is a hallmark of SCI. These data support and expand upon the work of others showing COX-2 as a relatively early response gene, with peak protein levels occurring as early as 6 hr after injury (Liu et al., 1997; Adachi et al., 2005). Another NF-κB-dependent gene involved in SCI pathology, iNOS, also increases 24 hr after SCI. It was shown that iNOS mRNA levels increase as early as 1 hr after SCI (Nesic et al., 2001) and that iNOS protein levels increased as early as 12 hr after SCI, the earliest documentation of SCI-induced iNOS protein. Although there are other factors linked to NF-κB activation that determine pathophysiology after SCI (Lau and Yu, 2001), the SCI-induced increases in COX-2 and iNOS, because of NF-κB activation, contribute critically to neuronal losses after injury and resultant loss of function.

To establish the NF-κB binding specificity of the Cox-2 promoter NF-κB decoy, the present invention demonstrates binding of the Cox-2 promoter NF-κB decoy sequence only to p65 and p50 but not to c-Rel using supershift/immunodepletion assays, consistent with the observed post-SCI changes in neuronal nuclear NF-κB. The efficacy of decoy intervention on NF-κB activation after SCI was also measured. Two hours after injury and decoy injection, there was an average decrease of 75% in NF-κB activity in the p65/p50 targeted decoy-treated cords compared with the injured-only group or the injured group treated with scrambled decoys.

The specificity of the decoy treatment was further validated by a comparable decrease in NF-κB activity following the addition of p65 antibodies to the vehicle-treated group samples prior to EMSAs. This decrease was not as robust as that seen with the Cox-2 promoter NF-κB decoy-treated group, most likely because of the contribution of p50 to NF-κB activity changes induced by SCI. These results are consistent with the successful selective blockade of NF-κB in treatment of dermatitis, breast cancer, hypoxia-ischemia, carotid artery injury, coronary disease, myocarditis, and retinoblastoma (Feeley et al., 2000; Park et al., 2001; Yokoseki et al., 2001).

The present invention demonstrates that the Cox-2 promoter NF-κB decoy treatment diminished the early spinal cord injury-induced COX-2 increases. Because decoys can rapidly penetrate cells at the injury site as early as 30 min after injection and COX-2 mRNA and protein levels increase at 1 and 2 hr after SCI, respectively, it is not surprising that the effect of the p65/p50 targeted decoys on protein levels manifests itself early on after SCI.

The ability of COX-2 promoter NF-κB decoys to bind p65/p50 NF-κB preferentially would suggest that other gene promoters displaying similar consensus sequences that also bind p65/p50 would likewise be affected. For example, iNOS is also regulated by p65/p50 (Teng et al., 2002), and, although there were no significant changes in iNOS expression at 2 or 12 hr after SCI and decoy treatment, there was a significant decrease at 24 hr. It takes at least 12 hr to measure significant changes in iNOS levels after SCI, so up-regulation of iNOS protein levels was likely delayed in relation to the effect on COX-2. Taken together, the delayed effects of p65/p50 targeted decoy treatments 24 hr after SCI are in agreement with p65/p50 inducing COX-2 and iNOS after SCI. Because Cox-2 promoter NF-κB decoys preferentially bind p65/p50, they should also suppress other inflammatory genes, in contrast to interventions, such as RNAi, that target a specific gene. Thus, decoys are likely to be useful blocking agents of inflammatory transcriptional events that mediate delayed neuronal death after SCI or other CNS trauma.

The BBB score measures locomotor function (Basso et al., 1995). It considers range of motion, weight-bearing ability, and movement of hind limbs over time. The BBB scores after a 150-kDyne SCI showed a significant locomotor improvement within the first week following decoy treatment that persisted for 145 days, consistent with an actual improvement in locomotion and not a delay in pathology. This suggests that Cox-2 promoter NF-κB decoy treatment has a protective, not restorative, effect. With a more severe contusion injury (200 kDynes), there was no significant improvement in BBB scores for the decoy-treated group up to 70 days after SCI. The failure of the decoy treatment in severe spinal cord contusion likely is due to a greater energy depletion, increased inflammation, and shifts from energy-dependent apoptotic processes to cell death with necrotic characteristics.

Although the decoy treatment did not improve motor function at 200 kDynes, there was sparing from hypersensitization induced by SCI (at both 150 and 200 kDynes) in decoy-treated animals as measured by the mechanical force required to elicit a withdrawal (Chaplan et al., 1994; Christensen and Hulsebosch, 1997). Thus, although decoy treatment failed to ameliorate locomotor losses in the more severe impact group, it did decrease hypersensitization. These outcomes are consistent with the observation that SCI causes larger losses of ventral motor neurons compared with dorsal sensory neurons (Nesic et al., 2005), mirroring the observed pathophysiology of SCI with its greater detriment to locomotion vs. development of hypersensitivity. Therefore, the efficacy of any given treatment is likely to be different for the different outcome modalities, such as locomotion and hypersensitivity.

Given that GABAergic deficits can activate nociceptive pathways after SCI (Jasmin et al., 2004), it was hypothesized that GABAergic deficits play a role in the increased hypersensitization resulting from SCI at the level of sensory input to the CNS. The present invention demonstrates that the decoy treatment was neuroprotective to GABAergic neurons in laminae 1-3. Because the tests used for hypersensitization measure forepaw sensitivity, whose sensory systems (within the cervical enlargement) lie segments away from injury and injection site, it was both surprising and promising that a single, brief decoy treatment could ameliorate the induction of hypersensitivity after SCI. However, it is not known whether these effects are a result of central processing in the brain or sensory function at the site of injury, in the periphery, or at the level of peripheral input to the CNS.

In summary, the present invention demonstrates that SCI increases p65/p50 activity while decreasing c-Rel/p50 activity in injured spinal cord, which in turn stimulates Cox-2 and iNOS transcription. DNA decoy blockade of SCI-induced p65/p50 activity decreases injured cord COX-2 and iNOS protein levels and enhances locomotor recovery while alleviating hypersensitivity. Additionally, the present invention also demonstrates that treatment with IL-1ra ameliorates Cox-2 levels in contused rat spinal cord, decreases neuronal cell loss and allodynia and improves locomoter recovery.

The present invention is directed to a method for treating neuropathic pain in an individual, comprising the step of administering pharmacologically effective amounts of a IL-1 receptor antagonist (IL-1ra) to the Such an administration may block the NF-κB-mediated increase in inflammatory cytokines and enzymes, may decrease neuronal cell loss, may decrease allodynia, may improve locomoter recovery or a combination thereof. Examples of inflammatory enzyme may include but is not limited to COX-2, iNOS or both. The cause for neuropathic pain may include but is not limited to spinal cord injury.

The present invention is also directed to a method for treating neuropathic pain in an individual, comprising administering a compound that alters inflammatory cascade at the NF-κB level in the individual, thereby treating neuropathic pain in the individual. The inflammatory cascade may be altered by decreasing levels of NF-κB. The levels of NF-κB may be decreased by administering an antisense specific to nucleic acid sequence encoding the NF-κB, administering a compound that interferes with the three-dimensional structure of NF-κB or by mutating the nucleic acid sequence encoding NF-κB.

Alternatively, the inflammatory cascade may be altered by blocking binding site for Cox-2 on NF-κB, blocking binding site for NF-κB on Cox-2 or both. Further, the binding for Cox-2 on NF-κB, binding of NF-κB on Cox-2 or both may be blocked by administering an oligonucleotide targeted to Cox-2 binding site on NF-κB, an oligonucleotide targeted to NF-κB binding site on Cox-2, chemical inhibitors, peptide inhibitors or antibodies. Example of the oligonucleotide that blocks NF-κB binding on Cox-2 may include but is not limited to an oligonucleotide that binds the p65/p50 subunit of NF-κB. Examples of the Cox-2 promoter NF-κB binding oligonucleotide may include but is not limited to an oligonucleotide that has a sequence of SEQ ID NO: 1. Since the binding site of Cox-2 on NF-κB gene and NF-κB on Cox-2 gene is known, one can generate such oligonucleotides using methods that are routine in the art. Further, the alteration of the inflammatory cascade at the NF-κB level may block the increase in inflammatory cytokines and enzymes, may decrease neuronal cell loss, may decrease hypersensitization, may improve locomoter recovery or a combination thereof. Examples of the inflammatory enzyme may include but is not limited to COX-2, iNOS or both. Furthermore, the cause of the neuropathic pain may include but is not limited to spinal cord injury.

The present invention is further directed to a method for altering the inflammatory cascade in spinal cord injury, comprising modulating the inflammatory cascade at the IL-1 receptor level, downstream thereof at the NF-κB level or both. The inflammatory cascade at the IL-1 receptor level is modulated by administering pharmacologically effective amounts of an IL-1 receptor antagonist. Alternately, the inflammatory cascade at the NF-κB may be decreased by decreasing levels of NF-κB, blocking binding site for Cox-2 on NF-κB, blocking binding site for NF-κB on Cox-2 or a combination thereof. Further, the levels of NF-κB may be decreased by administering an antisense specific to nucleic acid sequence encoding the NF-κB, administering a compound that interferes with the three-dimensional structure of NF-κB or by mutating the nucleic acid sequence encoding NF-κB.

Furthermore, the binding for Cox-2 on NF-κB, binding of NF-κB on Cox-2 or both may be blocked by administering an oligonucleotide targeted to Cox-2 binding site on NF-κB, an oligonucleotide targeted to NF-κB binding site on Cox-2, chemical inhibitors, peptide inhibitors or antibodies. Examples of the oligonucleotide that blocks NF-κB binding on Cox-2 may include but is not limited to an oligonucleotide that binds the p65/p50 subunit of NF-κB. Such an oligonucleotide may include but is not limited to an oligonucleotide that has a sequence of SEQ ID NO: 1. The modulation of the inflammatory cascade discussed herein may block the increase in inflammatory cytokines and enzymes, decrease neuronal cell loss, decrease hypersensitization, improve locomoter recovery or a combination thereof. Examples of the inflammatory enzyme may include but is not limited to COX-2, iNOS or both. Examples of the cause of the neuropathic pain may include but is not limited to spinal cord injury.

The use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "compound" or "agonist" or "antagonist" means a molecular entity of natural, semi-synthetic or synthetic origin that either activates of blocks, stops, inhibits, and/or suppresses pathways activated by IL-1R or NF-κB. For instance, the agonist will activate the pathway while the antagonist will block, stop, inhibit, and/or suppress the pathway.

Although the decoy discussed herein is an oligonucleotide, the decoy may comprise a peptide. The peptide may be from 10 to 100 amino acids in length and may be from 10 to 15, 20, 30, 40, 50, 60, 70, 80 or 90 amino acids in length. In another embodiment, the peptide may be from 20 to 30, 40, 50, 60, 70, 80 or 90 amino acids in length. As used herein, inhibitors or compounds (which block or alter binding sites or which alter gene expression, for example) may include chemical inhibitors or peptide inhibitors or antibodies as inhibitors, for example (which can be identified in accordance with the references cited below).

In various embodiments, the invention employs oligonucleotides targeted to nucleic acids encoding the nuclear factor kappa B or its binding site on COX-2. The relationship between an oligonucleotide and its complementary nucleic acid target to which it hybridizes is commonly referred to as "antisense". Once the target site or sites have been identified, oligonucleotides are chosen which are sufficiently complementary to the target, i.e., hybridize sufficiently well and with sufficient specificity, to give the desired modulation.

In various embodiments of this invention, oligonucleotides are provided which are targeted to mRNA encoding the nuclear factor kappa B or its binding site on COX-2. In accordance with this invention, persons of ordinary skill in the art will understand that mRNA includes not only the coding region which carries the information to encode a gene product using the three letter genetic code, including the translation start and stop codons, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. The functions of mRNA to be interfered with include all vital functions such as translocation of the RNA to the site for protein translation, actual translation of protein from the RNA; splicing or maturation of the RNA and possibly even independent catalytic activity which may be engaged in by the RNA. The overall effect of such interference with the RNA function is to cause interference with gene expression.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases. It is also contemplated that the oligonucleotide used can be double stranded so it could be interpreted as a dimer molecule, a heterodimer since sequences must be complementary and the ends may be modified by changing phosphates in the backbone to sulfate.

The compounds and/or inhibitors used in the methods of the subject invention encompass any pharmaceutically acceptable salts, esters, or salts of such esters, or any other compound/inhibitor which, upon administration to an animal including a human, is capable of providing (directly or indirectly) the biologically active metabolite or residue thereof. Accordingly, for example, the disclosure is also drawn to prodrugs and pharmaceutically acceptable salts of the compounds and/or inhibitors used in the subject invention, pharmaceutically acceptable salts of such prodrugs, and other bioequivalents.

In regard to prodrugs, the compounds and/or inhibitors for use in the invention may additionally or alternatively be prepared to be delivered in a prodrug form. The term prodrug indicates a therapeutic agent that is prepared in an inactive form that is converted to an active form (i.e., drug) within the body or cells thereof by the action of endogenous enzymes or other chemicals and/or conditions. In regard to pharmaceutically acceptable salts, the term pharmaceutically acceptable salts refers to physiologically and pharmaceutically acceptable salts of the compounds and/or inhibitors used in the subject invention: i.e., salts that retain the desired biological activity of the parent compound and do not impart undesired toxicological effects thereto.

The oligonucleotides used in the method of the subject invention preferably are from about 8 to about 50 nucleotides in length. In the context of this invention it is understood that this encompasses non-naturally occurring oligomers, preferably having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the skill of the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

Given the known nucleic acid and amino acid sequences of nuclear factor kappa B and COX-2, one can design appropriate antisense molecules for use in the subject invention. Furthermore, by expressing the nuclear factor or COX-2 in a host cell, one can screen for suitable compounds and/or inhibitors for use in the subject invention. Drugs, such as peptide drugs, which inhibit or otherwise modulate the binding of nuclear factor kappa B to COX-2 can be made using various methods known in the art. Initially, a monoclonal antibody can be prepared which specifically hybridizes to NF-κB or COX-2, thereby interfering with binding. The monoclonal antibodies can be produced by hybridomas. A hybridoma is an immortalized cell line which is capable of secreting a specific monoclonal antibody. In general, techniques for preparing polyclonal and monoclonal antibodies as well as hybridomas capable of producing the desired antibody are well known in the art As used herein, the term "pharmacologically effective amount" or refers to an amount that results in an improvement or remediation of the symptoms of the disease or condition due to blocking of the signal transduction. Those of skill in the art understand that the effective amount may improve the patient's or subject's condition, but may not be a complete cure of the disease and/or condition.

The compound or antagonist described herein may be administered independently, either systemically or locally, by any method standard in the art, for example, subcutaneously, intravenously, parenterally, intraperitoneally, intradermally, intramuscularly, topically, enterally, rectally, nasally, buccally, vaginally or by inhalation spray, by drug pump or contained within transdermal patch or an implant. Dosage formulations of the composition described herein may comprise conventional non-toxic, physiologically or pharmaceutically acceptable carriers or vehicles suitable for the method of administration.

The compound or antagonist described herein may be administered independently one or more times to achieve, maintain or improve upon a therapeutic effect. It is well within the skill of an artisan to determine dosage or whether a suitable dosage of either or both of the compound or antagonist comprises a single administered dose or multiple administered doses. As is well known in the art, a specific dose level of a compound or antagonist for any particular patient depends upon a variety of factors including the activity of the specific compound employed, the age, body weight, general health, sex, diet, time of administration, route of administration, rate of excretion, drug combination, and the severity of the particular disease undergoing therapy. The person responsible for administration will determine the appropriate dose for the individual subject. Moreover, for human administration, preparations should meet sterility, pyrogenicity, general safety and purity standards as required by FDA Office of Biologics standards.

Administration of the compound or antagonist of the present invention will follow general protocols for the administration of therapies used in treatment of spinal cord injury taking into account the toxicity, if any, of the components in the compound, the antagonist or in the combination therapy. It is expected that the treatment cycles would be repeated as necessary. It also is contemplated that various standard therapies, as well as surgical intervention, may be applied in combination with the described therapy.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Animal Model for Spinal Cord Injury

Rats were housed in the Animal Resource Center at the UTMB, and typically allowed 3-5 days to acclimate after shipping. Anesthesia was administered before surgery (pentobarbital, 35 mg/kg, intraperitoneally) and deemed complete when there was an absence of a blink reflex and no response to a foot pinch. The animal's back was shaved and the area washed with the antiseptic betadyne. A laminectomy was performed over spinal segment T10. The spinal cord was injured using the Infinite Horizon (Louisville, Ky.) spinal cord contusion device set to maximal force of 150 kDynes (1 second dwell time) onto the cord at T10. After injury, muscle and fascia were sutured, and the skin fastened to close the wound. Sham and injured animals received analgesic buprenorphin (0.1 mg/kg) subcutaneously twice a day for 3 days, and are given the antibiotic baytril (2.7 mg/kg) subcutaneously twice a day until bladder function returns. A 2 ml bolus of saline is injected subcutaneously for proper hydration.

Example 2

Drug Delivery

IL-1ra administration: CNP-like behavior was measured in rats treated with three doses of IL-1ra (Kineret; Amgen): 750 ng/ml, 1.25 mg/ml and 149.25 mg/ml, or one dose of decoys with 3 time regimes. The lowest concentration of IL-1ra (750 ng/ml) was found to be neuroprotective and was shown to significantly attenuate mechanical allodynia. All doses were delivered i.t. with Alzet osmotic minipumps (rate: 1 µl/h) for 72 h. Rats received contusion and were treatment blinded as to the agent delivered.

Decoy Treatment: Decoy was administered immediately after the injury. A Hamilton microinjection syringe containing a beveled 26 gauge needle was mounted onto a Kopf stereotaxic apparatus and placed into the center of the contusion site at a depth of 1.8 mm to ensure that the needle bore was in center of the cord. A 2 µl (4.9 nmol/µl) of solution was administered at a rate of 0.2 µL/min. The needle was left in place for 10 min to allow for diffusion of "decoys," and then slowly retracted. Subsequent to this, muscle and fascia were sutured and the skin closed with surgical staples.

Example 3

Mapping the "Girdle" Zone of Mechanical Allodynia

The rat's skin was marked with a grid using an indelible marker. A von Frey filament (beginning at 5 gm force) was applied to each point on the grid. The area of vocalization responses was recorded on a rat map onto which the grid pattern had been superimposed. By increasing or decreasing the von Frey strength, a mechanical threshold could be determined that produces audible vocalization responses. Since animals do not normally vocalize such a response is interpreted to indicate a noxious stimulus (Xu, et al., 1992). In mapping the area of response, the number of vocalizations were recorded (Nv) and normalized by the following formulae: (Nv×100)/total number of applications. This number indicates the percent vocalizations out of the total number of applications. Dermatome maps of mechanical allodynia were made according to previous study (Hulsebosch et al., 2000). These data were compared between groups as means±SD to determine statistically significant differences. Naïve animals did not usually respond to a stimulus of 5 gm force, but most SCI rats did so, so this strength was used in a modified "up down method".

Example 4

Protein Extraction Protocols and Western Blot

Spinal cord segments were manually homogenized in ice-cold 20 mM Tris HCl (pH 7.4) containing 10% (w/v) sucrose, 200 mM mannitol, 20 U/mL aprotinin, 20 µg/mL leupeptin, 20 µg/mL antipain, 20 µg/mL pepstatin A, 20 µg/mL chymostatin, 0.1 mM phenylmethylsulfonyl fluoride, 10 mM benzamidine, 1 mM EDTA and 5 mM EGTA. Crude homogenates were sonicated for 15 s and centrifuged at 1000 g 10 min (4° C.). The pellet was washed by trituration in homogenization buffer, followed by centrifugation and resuspended in homogenization buffer (without sucrose) supplemented with 20% (w/v) glycerol. The supernatant fluid was then centrifuged at 54,000 g for 20 min (4° C.) to yield soluble (S2) and mitochondria-enriched pellet (P2) fractions. This subcellular fractionation protocol is from Martin et al., 2003.

Samples containing 20 µg of cytoplasmic proteins were boiled for 5 minutes in an equal volumes of sample buffer (100 mM Tris, pH 6.8, 250 mM 2-mercaptoethanol, 4% SDS, 0.01% bromophenol blue, 20% glycerol), placed on ice, and then loaded onto a polyacrylamide gel. The stacking gel was 4% acrylamide, prepared in 0.13M Tris, pH 6.8, and 0.1% SDS, and the separating gel was 10% acrylamide, prepared in 0.38M Tris, pH 8.8, and 0.1% SDS. Samples were separated by electrophoresis in Tris-glycine buffer at a constant current of approximately 45 mAmps. Proteins were subsequently transferred overnight to an Immobilon-P® membrane at 4° C., 25 volts, in a transfer buffer containing 20% methanol, 20 mM Tris, and 150 mM glycine, at pH 8. Membranes were reversibly stained with Ponceau S to assure even transfer of proteins, destained in water, incubated for one hour at room temperature in blocking buffer containing 5% powdered milk in TBS-Tween, then washed for 10 minutes in TBS-Tween. Membranes were subsequently incubated for one hour in primary antibody diluted in 50% blocking buffer in TBS-Tween, and washed for 15 minutes in TBS-Tween. Membranes were incubated in horseradish peroxidase-conjugated goat anti-rabbit IgG, diluted 1:5000 in 50% blocking buffer for one hour, then washed 3× in TBS-Tween for 15 minutes. Peroxidase activity was detected with the Amersham enhanced chemiluminescence lighting system (ECL). Membranes were incubated in ECL reagent for 1 minute, excess reagent drained, and the membranes exposed to X-ray film for 10 seconds to 1 min. Protein bands were quantitated using a densitometer. β-actin was used as an internal control for cytoplasmic fraction and cytochrome c oxydase was used as an internal control for mitochondrial fraction.

Example 5

Decoy Deoxyoligonucleotide Preparation

Unmodified complementary single-stranded deoxyoligonucleotides used in EMSA assays were synthesized by Sigma-Genosys (Woodlands, Tex.).

```
Cox-2 sequence:
5'-GGCAAGGGGATTCCCTTAGT-3';      (SEQ ID NO: 1)

IgG-κB sequence:
5'-TTGAGGGGACTTTCCCAGGC-3';      (SEQ ID NO: 2)

Scrambled sequence:
5'-CGATCATAGTATCTGCACTG-3';      (SEQ ID NO: 3)

Bcl-X_L sequence:
5'-TTTGTGGGGGTCTCCAGCAT-3'.      (SEQ ID NO: 4)
```

Chemically modified complementary single-stranded "decoy" oligonucleotides containing one phosphothioate group on both 5' and 3' end are synthesized by Sigma-Genosys (Woodlands, Tex.).

```
Cox-2 sequence:
5'-GGCAAGGGGATTCCCTTAGT-3';      (SEQ ID NO: 1)

Scrambled sequence:
5'-CGATCATAGTATCTGCACTG-3'.      (SEQ ID NO: 3)
```

Single-stranded oligonucleotides were annealed to their complimentary strand in sterile saline at a stock concentration of 4.9 nmol/µL. Fluorescein was added to the phosphothioated oligonucleotides at the 5' end to examine the decoy oligonucleotide distribution. NF-κB transcription factor consensus binding sequences within each oligonucleotide are underlined.

Example 6

Immunohistochemistry

Conventional immunocytochemical fluorescent methods, using ALEXA fluroprobes (Molecular Probes, Inc.), was used to localize caspase 3, COX-2, NF-κB proteins, inflammatory cytokines and cytological markers and determine cellular origin by co-localization. The fixative solution for these studies was 4% paraformaldehyde in 0.1 M phosphate buffer (7.4). Spinal cords were dissected and post-fixed in the same solution for 2 h. Tissues were sectioned at a thickness of 30 μm with a freezing microtome or 15 μm with a cryostat. Spinal cord sections were rinsed in phosphate buffer (pH 6.5) before incubation overnight with the primary antibodies; which were obtained commercially. Receptor primary antibodies were used in dilutions of 1:1,000-1:10,000 (adjusted empirically). The primary antibodies to GFAP (astrocytes; Chemicon), NeuN (neurons; Chemicon), neurofilament 200 (neuronal filament; Chemicon), CC1 (oligodendrocytes; Oncogene Science), TuJ1 (neuronal marker, Covance), OX42 (microglia; Chemicon), NF-κB and COX-2; Santa Cruz) were used. The primary antibodies were diluted in phosphate buffered saline (PBS) with 0.1% BSA for overnight incubation on the spinal cord tissues. After washing in PBS (pH 7.6) sections were incubated in the appropriate secondary antibody, either anti-mouse or anti-rabbit IgG (1:100, 30 min) conjugated to a flurophore. In case of double-labeling experiments to determine cellular identity, fluorescent labeling techniques were preferred. For double labeling, Avidin, Texas Red, IgG fluorescein and the ALEXA flurophores were used in combination. Immunocytochemical controls included sections processed without the primary or secondary antibody as well as negative and positive control tissue appropriate for the particular antibody. The specificity of the antibodies was confirmed by adsorption controls with excess antigen when available. With regard to NeuN and GFAP in combination with apoptosis studies, Yong et. al., 1998 demonstrated co-localization with these markers and TUNEL$^+$ cells.

Computer-Assisted Image Analysis: Immunocytochemical stain density in grey and white matter for cytokines, etc. was determined by computer-assisted quantitation. For example, changes in expression of IL-1R were visualized with immunocytochemistry in contused rats and compared to sham-treated rats. Spinal cords were collected and stored frozen until all groups were completed. Then all tissues were cut and stained simultaneously. Since tissues were stained free-floating, they were randomly distributed on glass slides. The first five sections on a slide were tested. Background density readings were subtracted from each of the five readings, and the readings averaged to get a density value for each animal. The immunoreaction product was quantitated by computer-assisted image analysis using either NIH Image (density module software) or Metamorph. Images were captured from a Nikon FXA photomicroscope with an Optronics DEI-470 digitally enhanced color microscope video camera with built-in Digital Image Processor. A pentium Dell PC was the external computer used for the NIH image processing. Since tissues were rotated randomly on a rotator table during the staining procedure, it was assumed that their placement on the microscope slides was random. Stain density readings from each lamina from 5 sections/rat were averaged for that animal, and 5 rats sampled per group. Data were displayed as percent increase/decrease vs. control values.

Spared Tissue Calculations: (a) Volume Measurement—To measure lesion volumes, groups of animals were analyzed by measuring the areas of spared grey and white matter at the lesion site and at selected locations cranial and caudal to the epicenter so that the whole lesion was assessed, as in Wrathall, et. al., (1997). The protocols used offer a precise measure so both the volume and the shape of the contusion lesions can be accurately estimated in an unbiased way.

(b) Cell Counts—To determine numbers of labeled cells (GABA-stained lamina I-III neurons), stereological methods were used to obtain unbiased estimates of cell numbers. Cell counts were carried out blind on samples prepared and systematically sampled to achieve unbiased estimates (Coggeshall and Lekan, 1996). To determine numbers of GABA cells in lamina II and other superficial laminae of the dorsal horn in segment T8 of spinal cord, the cord containing T8 was serially sectioned transversely. The sections were taken in a uniform random pattern, i.e every $10^{th}$ section, and stained appropriately for GABA. The laminar boundaries on the chosen sections were outlined (If the boundaries were difficult to see, the facing sections were stained with a Nissl stain so they could be seen clearly). An appropriate sampling space on each section was selected (if only a few cells could be seen in a lamina, one could sample the whole lamina without difficulty. If as is more common, there were enough cells that this was impractical, sample spaces of appropriate sizes were selected so as to get a reasonable count). The numbers of cells in each sample space in each chosen section was counted by the optical dissector.

In brief, an upper and lower optical boundary in each sample space was chosen and the numbers of cells that come into focus between these boundaries were counted and added. The total cell numbers in the reference space was determined by multiplying total counts by the reciprocals of the sampled spaces, i.e. if every $10^{th}$ section was counted multiply by 10 and if the 25% of the volume of each section was sampled multiply by 4 for a total factor of 40. This procedure gave an unbiased estimate of numbers of GABA or any other cell types in the reference space (lamina II of T8). Since section separation and regions to be sampled vary in concert with the numbers of identified cells and with the experimental procedure, the general rule of thumb was that approximately 200 counts would reduce intra-animal variances to less than 5% (an intra-animal variance was the variation that occurred if one was to sample the same tissue over and over), so that one could get maximal clarity of a comparison between experimental and control groups.

Indentification of Neural Cell Types: Since it was necessary to identify neural cell types (neurons, oligodendrocytes, microglial, etc.) with the distribution of a protein of interest (receptor, transcription factors, etc), immunocytochemical procedures using cell-specific "markers" unique to that population of cells were used. These markers were labeled with fluroprobes that could be used to co-localize the protein of interest.

Double immunofluorescence staining: Animals were perfused with 2.5% glutaraldehyde, 0.5% paraformaldehyde in 0.1 M phosphate buffer via the aorta. The thoracic spinal cord T8 segments were removed, postfixed for 4 hours at 4° C., cryoprotected in 30% sucrose in phosphate buffer for two days, and embedded in OCT compound. Tissue sections were cut transversely at 30 mm on a sliding microtome. For immunofluorescence staining, floating tissue sections were rinsed (3×, 10 min, PBS) and incubated with 5% normal goat serum in PBS containing 0.01% Triton-X (PBST) for 60 min. Sections were rinsed with PBST 3×10 min and incubated with an antibody mixture of mouse anti-GABA (1:400, mouse monoclonal anti-GABA, Clone GB-69, Sigma) and rabbit anti IL-1RI (1:300, rabbit polyclonal antilL-1RI, M-20, Santa Cruz) followed by goat anti-rabbit IgG AlexaFluor 568 and goat anti-mouse IgG AlexaFluor 488 (Molecular Probes) diluted in PBST 1:500 for 4 h at room temperature. After rinsing 3×, 10 min with PBST, the double-stained tissue sections were mounted on gelatin-coated glass slides, dried, and coverslipped with non-fade media. Omission of the primary antibodies or use of non-specific secondary IgG's in the immunostaining process should result in no staining.

Example 7

Bisbenzimide Stain (Hoechst)

This procedure is described in Qiu et al., 2001b. Briefly, frozen sections were warmed to room temperature and placed in Tris buffered saline (TBS) for 5 min×2. Sections were stained with the fluorescent dye Hoechst 33342 (bisbenzmide) at 5 μg/ml for 5 min at 37° C. in the dark, and then observed under epifluorescence with a PloemPak filter (excitation/emission 340/465 nm) using a Leitz Optivert microscope. Apoptosis was assayed by TdT-mediated dUTP nick-end Labeling (TUNEL) assay. TUNEL assays were performed using an in situ cell death detection kit obtained from Boehringer Mannheim, according to the manufacturer's instructions. All samples were analyzed by flow cytometry in a Coulter Epics Elite.

Example 8

Electrophoretic Mobility Shift Assays (EMSA)

Oligonucleotides encompassing the IgG-κB enhancer sequence (GGGACTTTCC; SEQ ID NO: 5), iNOS and active COX-2 NF-κB binding DNA were used as probes and 5' labeled with $\alpha$-$^{32}$P-ATP and T4 polynucleotide kinase. Binding reactions with 10 μg of nuclear extract were performed in a 20 μl volume containing 20,000 cpm of probe, 2 μg of poly dI-dC, 10 μl of TK100 buffer (25 mM HEPES, pH 7.9, 20% glycerol, 1 mM EDTA, 100 mM KCl, 2 mM $MgCl_2$, 2 mM DTT, and 2 mM PMSF) and competitor as indicated. Nuclear extracts were incubated with poly dl-dC on ice, 10 min, followed by addition of buffer and probe. Incubation continued for 20 min at r.t. The mixtures were then loaded on 5% nondenaturing polyacrylamide gels in 0.25×TBE buffer (pH 7.2), gels dried and radioactivity measured. When antibodies were used for immunodepletion/supershift study, nuclear extracts were incubated with different antibodies for 30 min at 4° C. before addition of poly dl-dC. All antibodies, except p52 (Upstate Biotechnology, Cat. 06-413), were purchased from Santa Cruz Biotechnology (NF-κB c-Rel, SC-6955x; NF-κB p65, SC-372x; NF-κB p50, SC-7178x; NF-κB Rel-B, SC-226x). The methodology followed herein is a modification of the method described in Glasgow et al., 2000.

Example 9

Statistical Analyses

Statistical analyses for computer-assisted quantification of immunohistochemical staining was performed with one-way analysis of variance and Scheffe's post-hoc comparisons ($p<0.05$) with a minimum of 3 animals per group. Differences between groups were compared using two tailed Student's t-test ($p<0.05$). The number of animals for each experiment was based on power analyses carried out by UTMB Biostatistics Division. It was observed that for quantitative EMSAs, cell death ELISAs, and Western blot analyses, a minimum of 4 animals per group was necessary to obtain $p<0.05$. Differences in means among groups following time courses were analyzed using a two-factor analysis of variance (ANOVA) and repeated measures in which one factor was treatment group and the other was time of sacrifice. Post-hoc group comparisons at each time point were made using Tukey's HSD test. If the data did not follow a normal distribution, results were compared using non-parametric rank-based tests. Data were presented as means±SEM or SD.

Example 10

SCI Results in IL-1β-Mediated GABAergic Losses in Lamina II Neurons

The present invention examined relative IL-1R relative levels and distribution in GABAergic neurons after SCI. IL-1β binds to the IL-1 type-I receptor (IL-1RI), which then associates with an IL-1 receptor accessory protein (IL-1RAcP; Wesche et al. 1997) leading to signal transduction. It was observed that IL-1RI robustly expressed in spinal neurons in injured and uninjured spinal cords and astrocytes, with lower levels in microglia, oligodendrocytes, and endothelia (not shown). Furthermore, it is demonstrated herein that there is IL-1R expression by $GABA^+$ cells in laminae II (FIG. 1). Thus, there were $GABA^+NeuN^+$ cells (yellow); also non-neuronal $GABA^-$ cells and non-$GABA^+$ neurons, consistent with the known heterogeneity of GABAergic cells in lamina I-III (Heinke et al., 2004).

Example 11

Characterization of Decrease in GABA after SCI in IL-1R+GABAergic Cells

The well-characterized rat model of moderate spinal contusion (Gruner, 1992; Basso et al., 1995) is similar to the contusion/cyst type of injury prevalent in a clinical setting (Bunge et al., 1993). The present invention characterized much of the neuronal cell death resulting from contusion injury in the model and worked with two pain relevant models: first, where a proportion, but not all injured rats, developed pain (40-60%), and a second, where all rats develop pain (150 kDynes; 1 sec dwell time).

Work with the first model was useful in the attempts to get some information as to both the cellular (activated glia) and molecular pathways (angiogenesis, apoptotic signaling molecules) involved in some aspects of pain, as defined in the experimental model. However, for a thorough characterization of early causal events resulting in pain after SCI, it became necessary to focus on the second model where all animals develop pain. This is in part because SCI-induced hypersensitivity (girdling), the preferred assay for CNP, takes about two weeks to manifest itself after SCI. For the tissue immunocytochemistry and girdling assays, the present invention concentrated on the contused rat spinal cord segment (T10) and rostral segments (T8, T9), which corresponded to segments that clinicians usually describe as "at level pain".

Traumatic injury to the spinal cord has been reported to result in widespread apoptotic cell death of neurons and glia (Crowe et al., 1997). These apoptotic features were observed at 1 and 3 days after contusion SCI, using an immunoassay for the presence of cytoplasmic histone-DNA complexes, an assay for caspase-3 activity, and an in situ assay for the presence of Klenow fragments, a fairly selective apoptotic measure (Nesic et al., 2001). The findings presented in the present invention are consistent with reports of cytochrome c-dependent caspase-3 activation in neuronal and oligodendroglial cell death after rat and human SCI (Emery et al., 1998; Springer et al., 1999).

To measure cell death after SCI with the IH device, an ELISA was performed to detect cytoplasmic DNA-histone complexes. Fragmentation of DNA was measured by a cell death detection ELISA assay, which detects DNA fragmentation specific for nucleosome-associated cytosolic DNA. A significant cell death at the site of injury was observed as early as 12 h and up to 72 h after SCI (one-way ANOVA; FIG. 2).

To determine the neuronal loss after SCI over time, the levels of expression of the neuronal marker, NeuN, a 46-48 kDa protein present in the CNS and peripheral nervous system (PNS) neuronal nuclei were measured. The specificity of the marker was demonstrated previously by showing that NeuN was only present in neuronal populations residing in spinal cord gray matter. Immunocytochemical analyses of spinal cord tissue cross-sections at the injury site showed a ~50-80% decrease in neuronal cell numbers at 24 h; vs. sham controls at 24 h (Nesic-Taylor et al., 2005). To measure NeuN levels after SCI over time, the present invention compared Western blot assay analyses of nuclear protein from injured and age-matched sham-treated rats after 2, 12 and 24 hours (FIG. 3). There were significant decreases in NeuN levels at the site of injury at all three time points.

The present invention characterized cell death in the whole cord, with some delineation of differences among dorsal vs ventral areas, grey vs white matter, and rostral vs caudal segments in terms of the molecular participants in the inflammatory and cell death sequealae. The hypothesis was restricted to GABAergic action in laminae I, II, III of the dorsal horn at T8. That is, it was hypothesized that the mechanisms shown at work in the injured segments at level and the neurons present there are also at work in the GABAergic interneurons of laminae I-III, in the first rostral uninjured segment (T8), which plays a role in the development of CNP. Initially, it was proposed that SCI results in GABAergic neuronal losses, although an equivalent hypothesis would be that it is the function of the neurons that is impaired (that is, they are not absent, they simply do not synthesize or release GABA).

The GABAergic neuronal population was identified with two different antibodies (GABA and GAD67). Obtaining good images of GABA is difficult due to high background. Furthermore, since GABA is an amino acid, one must use high concentrations of glutaraldehyde to "fix" the tissue so as to keep a mobile molecule like an amino acid from escaping. This caused difficulties when trying to co-localize GABA with other compounds, as glutaraldehyde often impairs other antigen-antibody reactions. Nevertheless, images useful for counting of cells were obtained (FIGS. 4A-4B). Additionally, antibodies to GAD67, the rate-limiting enzyme for GABA production was also used. There are two forms of GAD: GAD65 and GAD67, both of which can respond to injury paradigms differentially (Moore et al., 2002). While the anti-GAD is compatible with other antibodies, it yields diffuse cellular images useful to ascertain levels in specific regions (see decrease in GAD67 staining in laminae II in contused cord vs. sham-treated in FIG. 4C), but not reliable for cell counting, but works well in Western blot assays (FIG. 4C). The preliminary data was consistent with decreased GABAergic expression 24 h after contusion, most notably in Lamina II. This could be due to a smaller number of spared GABAergic neurons after SCI or to decreased GAD expression in GABAergic cells due to a phenotypic change, for example if membrane transport properties are altered by injury, or both.

Example 12

Blocking SCI-Induced IL-1 Signalling Attenuated SCI-Induced Inflammatory NF-κB Activation, COX-2 Increases and Cell Death in GABAergic Neurons and CNP Development Affymetrix DNA microarray experiments and Western blot assays have shown that an early robust event after SCI was the expression of several cytokines and chemokines as part of a sequence of molecular events with inflammatory earmarks (Nesic et al., 2001; 2002). Not surprisingly, the earliest of the induced inflammatory cytokines to appear was IL-1beta (FIG. 5).

The present invention used confocal microscopy to evaluate the effect of IL-1ra on the GABAergic neurons. Briefly, confocal microscope stereology is the most accurate way to count actual cells rather than profiles. One can get 2 focal planes in one section a known distance apart and count only those objects that come into focus between these 2 planes. The only difficulty is to determine how much of the original population is sampled so that one can estimate the total numbers of cells. This is done using the fractionator where one takes the reciprocals of the ratios of sampled to total regions. Merged images display both GABAergic and non-GABAergic neurons. As shown in FIGS. 6A-6B, there was a significant increase in the number of spared GABAergic neurons in laminae I-III from contused rats treated with IL-ra.

Further, the vehicle-treated SCI group was compared to IL-1ra-treated (750 ng/ml, intrathecal delivery 1 µl/h, 3 days) group and to shams (N=5). As shown in FIG. 7, the SCI group had significantly lower thresholds compared to shams (*$p<0.05$) and to the presurgical data (not shown but not significantly different from shams); SCI+IL-1ra showed $p<0.05$ significant increase compared to vehicle-treated SCI. Data shown has mean±standard error that translates to a higher threshold of allodynia response or could be interpreted as higher pain threshold, hence less neuropathic pain.

Example 13

Consequences of IL-1ra Blockade on SCI-Induced NF-κB Activation of COX-2 Transcription It is know that IL-1 binds IL-1R in neuronal populations, resulting in stimulation of NF-kB p65 induction of inflammatory effectors (COX-2, iNOS) that result in a secondary wave of cell death with apoptotic features. The early decreases in c-Rel activity in injured tissues early after SCI (Qiu et al., 2001) were confirmed by measuring cytoplasmic protein levels of the NF-kB inhibitor IkB (FIG. 8). When the NF-kB expression was examined using confocal microscopy in the dorsal and ventral horn of contused spinal cords, a consistent pattern of change in different NF-kB proteins: c-Rel, p65, p50, p52, Rel B in neurons identified with NeuN was observed (FIGS. 9, 10). Western blot analyses of injured segments showed a dramatic decrease in c-Rel levels in nuclear fractions, an index of activation. While p65 increases were demonstrable, they were not significant, reflecting the heterogenous nature of whole segments. Because of the presence of non-neuronal glial cells, endothelial cells and invasive monocytes, the immunocytochemical identification of NF-kB cellular occupancy is considered herein as a more reliable index of post-SCI events. The results discussed herein are clearly consistent with a decrease in the anti-inflammatory or anti-apoptotic c-Rel activators, and with increased inflammatory p65 activators.

Further, NF-kB p65 has been implicated in the promotion of cell death associated with NF-κB activation. Injured spinal cord double-stained with NeuN and p65 or p50 antibodies showed increases up to 24 hours after SCI, but not at 7 days, with no appreciable changes in oligodendroglial levels. Bethea (2000; Bethea et al., 1998) reported increases in p65 after SCI using EMSA tissue analyses, which did not identify the cellular phenotypes involved. Dimerization of p50 with p65 is associated with progression of cell death (Grilli et al., 1996), while dimerization with c-Rel is thought to stimulate cell survival mechanisms. When p52 and RelB were measured herein using immunocytochemistry, no noticeable changes in the neuronal or oligodendroglial levels of p52 or RelB were observed. Since c-Rel NF-kB upregulates Bcl-2, Bcl-xL, MnSOD and other anti-apoptotic molecules and p65 upregulates pro-apoptotic COX-2, iNOS, IgG, IL-6 and other inflammatory cytokines and chemokines, the preliminary results suggest that the observed SCI-induced shift in the neuronal NF-κB balance determines whether NF-κB activation leads to survival or apoptosis.

The novel finding of an IL-1R presence on GABAergic neurons (FIG. 11D) and amelioration of COX-2 levels in contused rat spinal cord treated with IL-1ra (FIG. 11C) is consistent with the hypothesis that IL-1 inflammatory signaling via IL-1R triggers NF-kB-mediated increases in inflammatory cytokines and enzymes such as COX-2 and iNOS. There is evidence showing a causal relationship between COX-2 and neuropathic pain. The action of both COX-2 and iNOS has been shown to generate peroxynitrates and hydroxyl radicals, known to exacerbate oxidative stress and so stimulate cell death with apoptotic features. A significant early and lasting up-regulation of Cox-2 mRNA was observed starting from 1 h after SCI and lasting for at least 24 h after injury, supporting work by others showing Cox-2 is an early response gene.

To determine how increases in mRNA translate to changes in COX-2 protein levels, the changes in Cox-2 protein levels after SCI in injured rats were measured by Western blot analysis at the site of injury (FIG. 11A). There was a sevenfold increase in Cox-2 protein expression at the site of injury up to 3 days after SCI. The timing of changes in Cox-2 levels correlates with cell death in peri-lesion sites hours and days after SCI (Liu et al., 1997), explaining in part the pathogenesis due to SCI. Another NF-κB-dependent gene involved in the pathology of SCI is iNOS. Increases in iNOS protein levels are apparent in SCI rat cords after 24 hours; these increases have been implicated in the pathogenesis associated with traumatic SCI. The iNOS protein levels increased after SCI, another source of neuropathology (FIG. 11B). This latter finding has added significance given the regulatory effects of iNOS on COX-2.

Example 14

Blockade of SCI-Induced COX-2 Increases with Decoy Oligonucleotides Targeted to the COX-2 Gene Promoter and Ameliorates Inflammation and CNP Effects of NF-κB decoys targeted to the COX-2 promoter on COX-2 levels in GABAergic neurons after SCI: NF-κB subunit-specific inhibition can be accomplished with synthetic double-stranded "decoy" deoxyoligonucleotides containing a specific NF-κB consensus sequence (Bassett et al., 2004; Cho-Chung et al., 1999). Fluorescein-tagged decoys were injected into spinal cord injury to determine stability, cellular occupancy and duration of decoy integrity.

Decoy penetration into spinal cord tissue was observed as early as 30 minutes after injection, with strong nuclear localization at both 2 and 4 hours; by 7 hours there was a significant decrease in fluorescence (FIG. 12). More specifically, co-localization of decoys in the nucleus was observed after 2 h, and localization within the cytoplasm of spinal cord cells was observed after 4 h. Seven hours after injection, the signal was noticeably decreased, presumably due to degradation of the decoys. Dispersion of decoys was seen in the rostral and caudal segment by 2 hours. Based on this, a predictable time window during which decoys could block NF-κB activation was established that correlated well with similar interventions in the hippocampus of post-natal day 7 rat pups after hypoxia/ischemia injury (Qiu et al., 2004).

Figure 13:
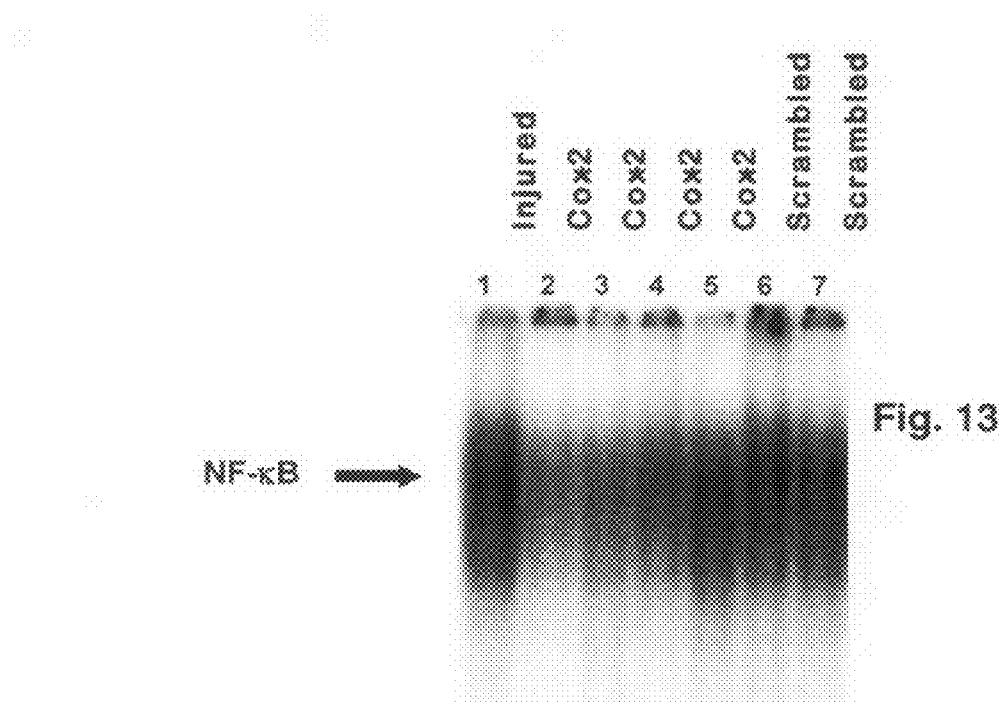
FIG. 13 shows the effects of Cox-2 promoter NF-κB on NF-κB activation after spinal cord injury. EMSA analysis of nuclear NF-κB binding to the COX-2 promoter sequence (GGGGATTCCC; SEQ ID NO: 6) 2 h after spinal cord injury and treatment is shown. Treatment with COX-2 promoter NF-κB decoy after spinal cord injury decreases NF-κB activation. Lane 1: injured cord, lanes 2-5: injured cord injected with COX-2 promoter NF-κB decoy, lanes 6-7: injured cord injected with scrambled decoy. Numbers reflect the percent decrease compared to the injury alone group using densitometric analysis.

To test how well the Cox-2 promoter NF-κB decoy sequence binds NF-κB, electromobility shift assays (EMSAs), which measures binding between radioactively labeled decoy probes and nuclear protein extracted from spinal cord were used. Protein extracted from injured spinal cord was used to compare control cord, cord injected with Cox-2 promoter NF-κB decoy and cord injected with a scrambled decoy. Two hours after injury and decoy injection, there was a decrease in the activation of NF-κB in the Cox-2 decoy-treated spinal cord compared to both the injured only group and the injured group treated with scrambled decoys (FIG. 13). The activation of NF-κB after injury was comparable between these two control groups (FIG. 13, lanes 1, 6 and 7).

Figure 14:
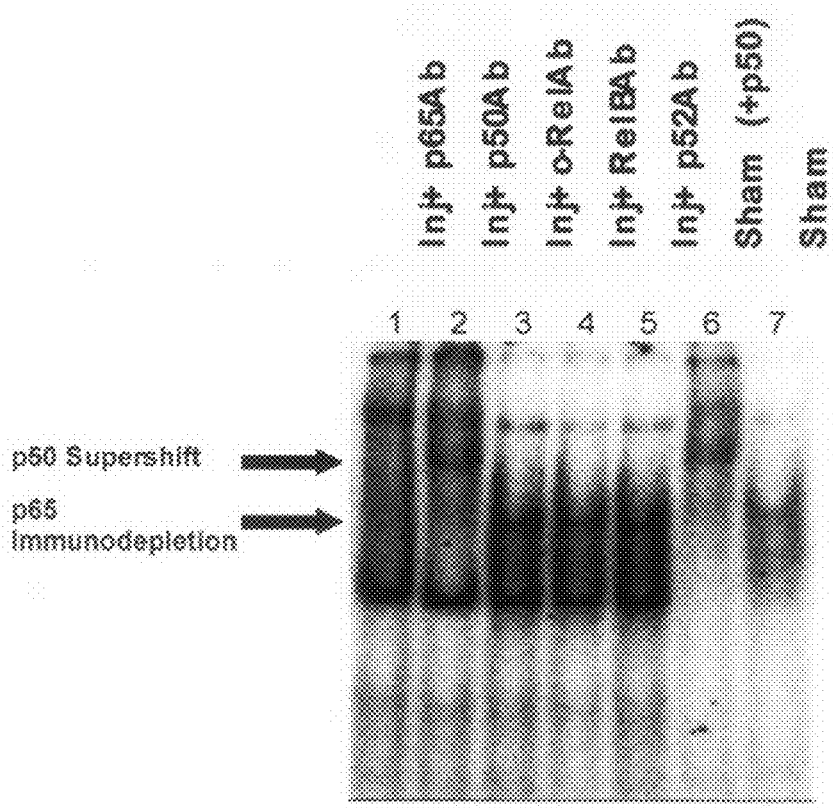
FIG. 14 shows binding specificity of COX-2 promoter NF-κB decoys to NF-κB p50/p65. EMSA analysis of nuclear NF-κB subunit binding to the Cox-2 promoter sequence (GGGGATTCCC; SEQ ID NO: 6) 2 h after spinal cord injury is shown. Supershift/immunodepletion shows binding of only p65 (lane 1) and p50 (lane 2) to the COX-2 promoter sequence. The lack of changes in the other subunits (lanes 3-5) validates this specificity. Activation of NF-κB after SCI is demonstrated by increased signal in injured (lanes 1-5) versus sham cord (lanes 6-7). Lane 1: Injured cord+p65Ab, Lane 2: Injured cord+p50Ab, Lane 3: Injured cord+c-Rel Ab, Lane 4: Injured cord+RelB Ab, Lane 5: Injured cord+p52 Ab, Lane 6: sham-treated+p50, Lane 7: sham-treated cord.

It was important to establish the NF-κB subunit-binding specificity of the Cox-2 promoter NF-κB decoy, to achieve selective intervention in the post-SCI inflammatory process. Specific subunits that the Cox-2 promoter NF-κB decoys would bind were examined by adding antibodies to all 5 NF-κB subunits in the EMSAs. The presence of specific subunit was detected by supershift or immunodepletion of bands compared to the same bands without antibodies. FIG. 14 shows binding of the Cox-2 promoter NF-κB decoy sequence only to p65 (lane 1, immunodepletion) and p50 (lane 2, supershift), and not to RelB, c-Rel or p52 (lanes 3-5). Activation of NF-κB after SCI was demonstrated by increased signal in the injured (lanes 1-5) vs. sham-treated (lanes 6-7) cords.

In order to determine whether Cox-2 promoter NF-κB decoys abrogate the up-regulation of their target gene over time, the COX-2 protein levels in injured animals injected with Cox-2 promoter NF-κB decoys and scrambled decoys (control) were measured immediately after SCI. There was a decrease in Cox-2 expression at the injury site in the Cox-2 promoter NF-κB decoy-treated group compared to scrambled decoy injected rats at 2 hours. This decrease was not observed 12 hours after injured spinal cords were injected with the Cox-2 promoter NF-κB decoy (FIG. 15).

Since iNOS expression is also regulated by NF-κB, the present invention examined the effects of Cox-2 promoter NF-κB decoys over time (FIG. 16). Although there were no significant changes in iNOS expression at the injury site at 2 or 12 hours, there was a significant decrease in iNOS protein after 24 hours in the Cox-2 promoter NF-κB decoy-treated group compared to the scrambled decoy-treated group. Since up-regulation of iNOS protein levels by SCI is delayed vs. that of COX-2 after SCI, it is not unexpected that the predicted effects of decoys would be also delayed.

Figure 17:
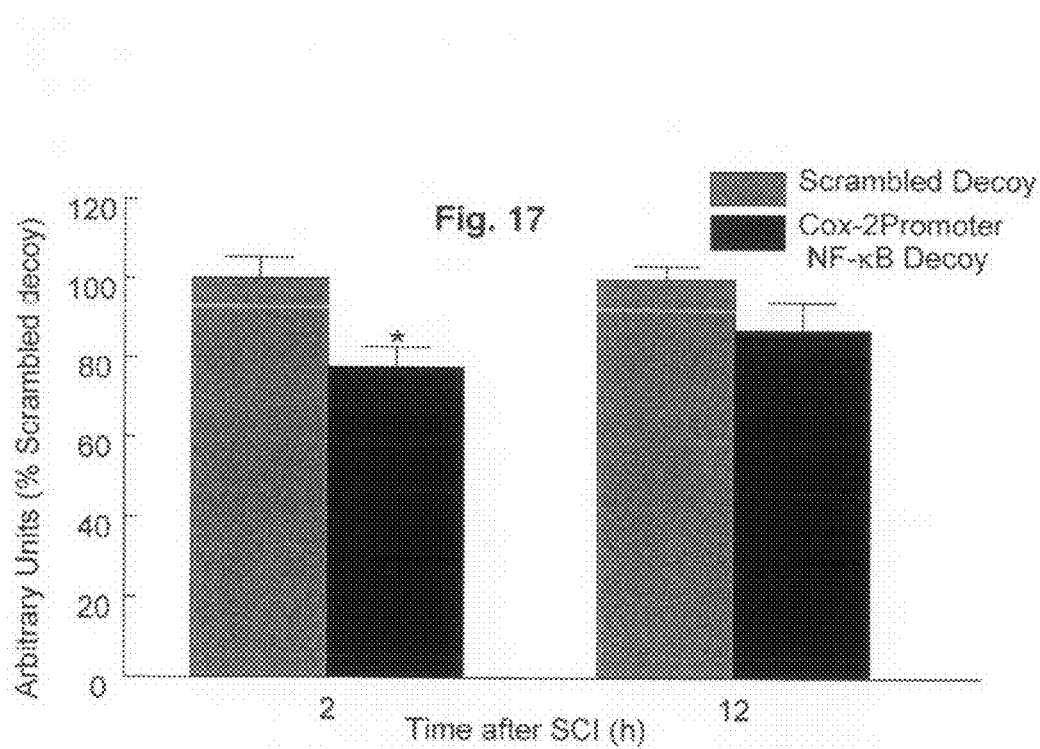
FIG. 17 shows effects of Cox-2 promoter NF-κB decoy on IκB-α protein expression after SCI. Western blots were used to analyze the injury site for cytoplasmic levels of IκB-α protein in Cox-2 promoter NF-κB decoy (black bars) and scrambled decoy treated rats (gray bars) at 2 and 12 h (n=4 for 2 h group, n=5 for 12 h group). Values are ±SEM normalized to sham group (not shown). *p<0.05 compared to age-matched sham-treated group (two-tailed Student's t-test). Representative blot is shown.

Although IκB-α is known to be degraded as a means for the activation of NF-κB, it is also an immediate target of NF-κB p65/p50. Hence, there is a negative feedback regulatory pathway whereby activation of NF-κB leads to synthesis of IκB-α inhibitor proteins. To determined how decoy injections would affect expression of IκB-α over time, the IκB-α protein levels from the injury site at 2 and 12 hours were measured (FIG. 17). IκB-α protein levels in injured spinal cords injected with Cox-2 decoys were compared to IκB-α protein levels in injured spinal cords injected with scrambled decoys (control). Significant decreases in IκB-α protein levels were observed at 2 hours but not at 12 hours.

Figure 18:
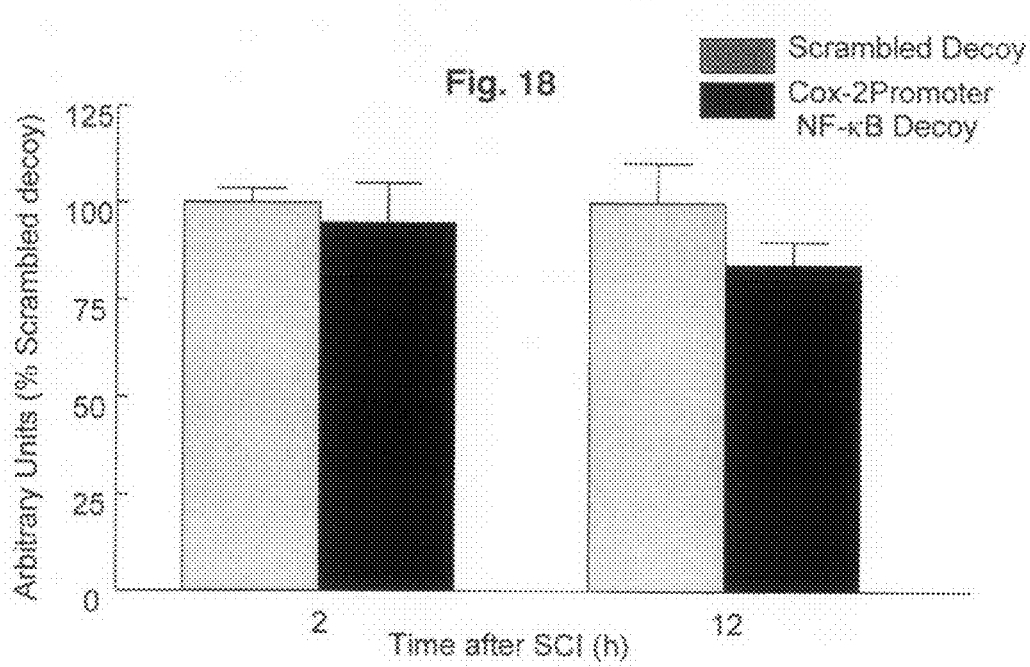
FIG. 18 shows effects of Cox-2 promoter NF-κB decoy on IκB-α protein expression after SCI. Western blots were used to analyze the injury site for cytoplasmic levels of IκB-α protein in Cox-2 promoter NF-κB decoy (black bars) and scrambled decoy treated rats (gray bars) at 2 and 12 h (n=4 for 2 h group, n=5 for 12 h group). Values are ±SEM normalized to sham group (not shown). *p<0.05 compared to age-matched sham-treated group (two-tailed Student's t-test). Representative blot is shown.

Another inhibitory molecule of NF-κB p65/p50 activation is IκB-α. However, unlike IκB-α, IκB-α is not thought to be under the dominant control of NF-κB, especially after NF-κB activation. When the protein levels of IκB-α at the injury site were measured using Western Blot analysis, no significant changes associated with Cox-2 promoter NF-κB decoy intervention was observed on the IκB-α protein levels at either time points when compared to the scrambled decoy (FIG. 18).

Further, to measure the effect of decoy treatment of SCI on clinically relevant outcomes, the locomoter function was measured using the well-established BBB locomotor recovery scale (Basso et al, 1995) for up to 145 days after 150-kDyne force contusion SCI. There was a mean improvement of 2 BBB points (19.4 vs 17.5) in the Cox-2 promoter NF-κB decoy-treated group at the latest time point tested compared to the scrambled decoy-treated group (FIG. 19A). Thus, there was a significant improvement in locomoter recovery over time after the Cox-2 promoter NF-κB decoy-treatment compared to the vehicle-treated group. Examination of the differences in BBB score units between the two treatments of time showed a significant locomoter improvement as early as the first week after the Cox-2 promoter NF-κB decoy treatment relative to the scrambled decoy treatment (FIG. 19B), with no further locomoter advantage evident beyond the first week of treatment. This improvement conferred by the Cox-2 NF-κB decoy treatment persisted for 145 days.

To assess the range of efficacy of the decoy treatments, the effects of the decoy treatment after harsher 200 kDyne force contusion SCI was measured vy evaluating locomoter function in rats treated with Cox-2 promoter NF-κB decoy-treated animals compared to scrambled decoy-treated animals. FIG. 19C shows that there were no improvements in locomoter function in the rats exposed to the more severe contusion injury regardless of the treatment with decoys.

As the force of the contusion injury increases in this model, so does the level of hypersensitization (Basso et al., 1996). The present invention used standard measure for sensitivity to mechanical force (mechanical allodynia) in which increasing pressure is applied to forepaws of rats by von Frey hair filaments until they elicit a withdrawal response (Chaplan et al., 1994). Responses were assessed between injured rats treated with the Cox-2 promoter NF-κB decoy and the scrambled decoy for up to 10 weeks after a 200 kDyne force contusion SCI and compared with their preinjury baseline responses. FIG. 19D shows that there was a significant alleviation of hypersensitivity in the Cox-2 promoter NF-κB decoy-injected group compared to scrambled decoy-treated cohort.

Furthermore, to determine whether in GABA activity played a role in the decreased hypersensitivity resulting from the Cox-2 promoter NF-κB decoy treatment after SCI, GABA-containing neurons in the laminae 1-3 of Cox-2 promoter NF-κB decoy-treated cords were counted and compared to the scrambled decoy-treated cords. There were significantly more GABAergic neurons in the Cox-2 promoter NF-κB decoy-treated group at the T9 level (FIG. 20A). There was also a trend showing increased numbers of GABAergic neurons at the C7/C8 level (FIG. 20B) but no discernible differences at L4-L5 (data not shown).

Since the tests for CNP measure forepaw sensitivity, whose sensory systems (cervical enlargement) lie many segments away form the injury and injection site, it is both surprising and promising that a single, brief treatment can aid in prevention of certain hypersensitive states after SCI.

The following references were cited herein:
Spinal Cord Injury Information Network. University of Alabama at Birmingham.Facts and figures at a glance. June, 2005
Abbadie, C. et. al. (1993), Cell. 75(5): 899-912.
Adachi S. et al. (1997), J Biol Chem.; 272(35):21878-82.
Adams V. et al. (2002), Cardiovascular Research. 54(1):95-104.
Appleby, S. B. et al. (1994), Biochem. J. 302:723-727.
Bartholdi, D. and Schwab, M. E. (1997), Eur. J. Neurosci. 9(7): 1422-38.
Baeuerle P A. (1991), Biochemica et Biophysica Acta 1072: 63-80.
Barger S W and Mattson M P (1996), Mol. Brain Res., 40:116-126.
Bassett, S. E, S. M. et al. (2004), Biochemistry 43, 9105-9115
Basso, D. M. et al. (1995), J. Neurotrauma, 12:1-21.
Basso, D. M. et al. (1996), Exp. Neurol. 139: 244-256.
Beattie M. S. (2004), TIMM 10:580-583.
Beattie M. S. et al. (2002), Prog Brain Res; 137:3747
Bethea J R et al. (1998), J Neurosci., May 1; 18(9): 3251-60.
Bethea, J. R. et al. (1999), J. Neurotrauma 16, 851-863
Bethea J R. (2000), Prog Brain Res. 128:33-42. Review.
Baichwal, V R and Baeuerle, P A. (1997). Curr. Biol. 7(2): R94-R96.
Barger, S W et. al. (1995), Proc. Natl. Acad. Sci. U.S.A. 92(20): 9328-9332.
Blondeau, N. et. al. (2001), J. Neurosci. 21(13): 4668-4677.
Bours v. et. al. (1993a), Cell. 72729-739.
Bours, V et. al. (1992), Mol. Cell Biol. 12(2): 685-695.
Bours, V et. al. (1990), Nature. 348(6296): 76-80.
Brambilla, R et al. (2005). J. Exp. Med. 202, 145-156
Bundy, D L and McKeithan, T W. (1997), J. Biol. Chem. 272(52): 33132-33139.
Cao G. et al. (2002), J Neurosci; 22(13):5423-31
Cao X et al. (2002), Chinese J. Traumatol. 5:131-5.
Cao Z et al. (1996), Science 271, 1128-1131.
Chan, C. F. et al. (2000), Eur. J. Pharmacol. 402:61-68.
Chaplan, S. R et al. (1994), J. Neurosci. Methods 53, 55-63.
Chatzipanteli, K. et al. (2002), J. Neurotrauma 19, 639-651
Chakravarthy B R et al. (1999), J Neurochem; 72(3):933-42
Cho-Chung, Y. S. et al. (1999), Curr. Opin. Mol. Ther. 1, 386-392.
Chu, D. et al. (2002), Neurochem. Res. 27, 97-106
Christensen, M. D. et al. (1996), Pain 68: 97-107.
Christensen, M. D. and Hulsebosch, C. E. (1997) J. Neurotrauma 14: 517-537.
Coggeshall, R. E. and Lekan, H. A. (1996), J. Comp. Neurol. 364:6-15.
Coggeshall R E et al. (2001), J Comp Neurol. 435:276-82.
Conti, A. et al. (2003), J. Neurosurg. Sci. 47:89-94.
Crowe, M. J. et al. (1997), Nature Medicine. 3:73-76.
Crowe, M. J. et al. (1997), Nature Med. 3: 73-76.
De Novellis V et al. (2004), Neuropharmacol. 46:468-479.
deNovellis V et al. (2004), Neuropharmacology 46:468-479
Dinarello C. A. (1996), Blood 87, 2095-2147
Dixon, W. J. (1980), Annu. Rev. Pharmacol. Toxicol. 20, 441-462
Drew, G. M. et al. (2004), Pain. 109:379-388.
Dumont R J et al. (2001), Clin Neuropharmacol; 24(5):254-64.
Emery E. et al (1998), Journal of Neurosurgery 89, 911-20.
Fiebich, B. L. et al. (2000), J. Neurochem. 75:2020-2028.
Flower R J. (2003), Nature Rev. Drug Dev. 12:179-191.
Foster-Barber, A et al. (2001), Dev. Neurosci. 23(3): 213-218.
Franzoso, et. al. (1993), EMBO J. 12(10): 3893-3901.
Franzoso, G. et. al. (1992), Nature. 359(6393): 339-342.
Glasgow J N et al. (2001), Neurochem Res (6):647-59
Ghosh, S and Baltimore, D. (1990), Nature. 344(6267): 678-682.
Granados-Soto, V. et al. (2005), Pain, 114:231-238.
Grilli, M. et. al. (1996), J. Biol. Chem. 271(25): 15002-15007.

Grilli M et al. (1996), Science 274: 1383-1385.
Grilli, M and Memo, M. (1999), Cell Death. Differ. 6(1): 22-27.
Grimm, S. et. al. (1996), J. Cell Biol. 134(1): 13-23.
Grossman S D et al. (2001), Exp Neurol. 168(2): 273-82.
Gruner, J. A. (1992), J. Neurotrauma 9: 123-128.
Gwak Y. S. et al. (in press) Activation of GABAergic receptors attenuate central neuropathic pain after spinal cord injury.
Hains B. C et al. (2001), J. Neurotrauma 18:409-423.
Haskill, S. et. al. (1991), Cell. 65(7): 1281-1289.
Hayashi, M. et al. (2000), J. Neurotrauma, 17 (3): 203-218.
Heinke B et al. (2004), J Physiol. 2004 560(Pt 1):249-66.
Herman R M et al. (1992), Clin J Pain. 8:338-45.
Holmin, S. and Mathiesen, T. (2000), J. Neurosurgery, 92(1): 108-120.
Hu, Xiaoming et al. (2005) J. Neurochemistry 93:26-37.
Hulsebosch, C. E. et al. (2000), J. Neurotrauma 17: 1205-1217.
Igwe O J et al. (2001), Neuroscience. 105(4)::971-85.
Irmler M. et al. (1995), J Exp Med 81(5):1917-22
Israel, A. (1995), Trends Genet. 11(6): 203-205.
Jasmin L et al. (2004), Curr Drug Targets CNS Neurol Disord. 3:487-505.
Jung, S. et. al. (1995), Ann. N. Y. Acad. Sci. 766245-252.
Kaltschmidt, C. et. al. (1994), Mol. Cell Biol. 14(6): 3981-3992.
Kang, S M. et. al. (1992), Science. 256(5062): 1452-1456.
Kato, H. et al. (1997), Exp. Neurol. 148:464-474.
Katoh, K. et al. (1996), Neurosci. Lett. 216, 9-12.
Kaufmann, W. E. et al. (1996), Proc. Natl Acad. Sci. U.S.A. 93, 2317-2321
Kessler, J. A. et al. (1993), Neuron 11, 1123-1132
Kim, S. H. and Chung, J. M (1992), Pain 50: 355-363.
Kim S F et al. (2005), Science. 310:1966-1970.
Klusman, I. and Schwab, M. E. (1997), Brain Research 762: 173-184.
Koong, A C et al. (1994), Cancer Res. 54(6): 1425-1430.
Kossmann, H. et al. (1999), J. Cereb. Blood Flow Metab. 19(2): 184-194.
LaRosa, G. et al. (2004), J. Neurosurg. Spine 1:311-321.
Lau, L T and Yu, A C. (2001), J. Neurotrauma. 18(3): 351-359.
Lee, K. M. et al. (2004), Eur. J. Neurosci. 19:3375-3381.
Lipton, S A. (1997), Nat. Med. 3(1): 20-22.
Liu, J et al. (1993), Mol. Immunol. 30(5): 479-489.
Lebedeva T V and Singh A K. (1997), Biochim Biophys Acta 1353(1):32-8.
Lin, K. I et al. (1995), J. Cell Biol. 131, 1149-1161.
Liu, X. Z. et al. (1997), J. Neurosci. 17:5395-5406.
Liu X. Z. et al. (1997), Journal of Neuroscience 17(4), 5395-5406.
Lu C R et al. (2005), J Comp Neurol. 486:169-78.
Ma, W. and Bisby, M. A. (1998), Br. Res. 797:243-254.
Martin L J and Liu Z. (2002), J Neurobiol. 50(3):181-97.
McTigue D M et al. (1998), J Neurosci Res. 53(3):368-76.
Milligan E D et al. (2003), J. Neurosci. 23:1026-1040.
Moore K A et al. (2002), J. Neurosci. 22:6724-6731.
Morishita, R. et. al. (1997), Nat. Med. 3(8): 894-899.
Muzio M. et al. (1997), Science 278, 1612-1612.
Nakao Y et al. (2001), J. Thoracic & Cardiovasc. Surg. 122: 136-43.
Nesic, O et al. (2002), J. Neurosci. Res. 68: 406-423.
Nesic, O. et al. (2001), J. Neurotrauma. 18(9), 947-956.
Nesic-Taylor, O et al. (2005) J. Neuroscience Res., In Press, 79:628-637

Newton R et al. (1997), Biochem Biophys Res Commun., 237(1):28-32.
Nolan G. et. al. (1991), Cell. 64961-969.
Nolan, G P. et. al. (1993), Mol. Cell Biol. 13(6): 3557-3566.
O'Neill L A (2000), Sci STKE 44):RE1
O'Neill L. A. J. and Greene C. (1998), J. Leukoc. Biol. 63, 650-657
O'Neill L A and Dinarello C A. (2000), Immunol Today (5):206-9.
Pan J Z et al (2002), J Neurosci Res; 68(3):315-22
Pinteaux, Emmanuel et al. (2002), Journal of Neurochemistry 83 (4), 754-763.
Pizzi, M et. al. (2002), J. Biol. Chem. 277(23): 20717-20723.
Qiu J. G. et al. (2001), J. Neurotrauma, 18 (11) 1267.
Qiu J et al. (2001), J Neurosci Res 64(3):223-34.
Qiu, J et al. (2004), J. Neurosci. Res. 77(1): 108-18.
Ray S K et al. (2000), Brain Res. 867(1-2):80-9.
Ray S K et al. (2000), Neurochem Res. 25:1191-8.
Resnick D K et al. (1998), J Neurotrauma, 15(12):1005-13.
Rode F et al. (2005), Eur J Pharmacol. 516:131-8.
Rothwell N J et al. (1997), Int Rev Neurobiol. 40: 281-98.
Rothwell N J. (1999), J. Physiol. 514.1: 3-17.
Ruben, S M. et. al. (1991), Science. 254(5028): 11-15
Ryseck, R P. et. al. (1992), Mol. Cell Biol. 12(2): 674-684.
Sakaue, G. et al. (2001), NeuroReport 12:2079-2984.
Saliba, E and Henrot, A. (2001), Biol. Neonate. 79(3-4): 224-227.
Scheff S W et al. (2003) J. Neurotrauma 20: 179-193.
Schmid, R M. et. al. (1991), Nature. 352(6337): 733-736.
Schmidt, K N et. al. (1995), J. Biol. Chem. 270(45): 27136-27142.
Scholz J, et al. (2005), J Neurosci. 25:7317-23.
Sims J. E et al. (1988), Science 241, 585-588.
Sirenko, Oksana, et al. (2002), Immunology and Cell Biology 80 (4), 328-339.
Sokal D M and Chapman V. (2003), Br. Res. 962:213-20.
Springer J E et al (1999), Nature Neurosci. 5(8): 943-6.
Streit W J et al. (1998). Exp. Neurology 152: 74-87.
Svrakic, N. M et al. (2003) Statistical approach to DNA chip analysis. Recent Progress in Hormone Research, (eds. A.R. Means), 58, 75-93.
Tachibana T et al. (2005), J. Thor. Cardio. Surg. 129:123-128.
Tagialatela G et al. (1997), J. Neurosci. Res., 47:155-162.
Taira T et al. (1995), Stereotact Funct Neurosurg. 65:101-5.
Taoka Y and Okajima K. (1998), Prog Neurobiol.; 56(3): 341-58. Review.
Tegeder, I et al. (2004), J. Neurosci. 24:1637-1645.
Teng X et al. (2002), Am J Physiol Cell Physiol., 282(1): C144-52.
Thompson, J E. et. al. (1995), Cell. 80(4): 573-582.
Tomita, N et al. (1997), Exp. Nephrol. 5, 429-434.
Tonai T et al. (1999), J Neurochem., 72(1):302-9.
Topol E J. (2005) JAMA, 293:366-368
Turini E M and DuBois R N. (2002), Ann. Rev. Med. 53:35-57.
Van Antwerp, D. J et al (1996), Science 274, 787-789
Volk, D. E. et al. (2002), Bioorg. Chem. 30, 396-419.
Wang, C X et al (1997), Brain Res. 759(2): 190-196.
Weng H R and Dougherty P M (2005), Neuroscience. 132: 823-31.
Wesche H et al. (1997), J. Biol. Chem. 272, 7727-7731.
Whiteside G. T and Munglani R. (2001). Cell death in the superficial dorsal horn in a model of neuropathic pain.
Wiesenfeld-Hallin Z et al. (1997), Behav Brain Sci. 20:420-5
Willis, W. D. Jr. and Coggeshall, R. E. Sensory Mechanisms of the Spinal Cord. Vol. 1 and 2, Kluwer Acad. Plenum Publ., New York, 2004

Wingrave J M et al. (2003), J. Neurosci. Res. 73:95-104.
Wrathall, J. R et al. (1994), J. Neurosci. 14:6598-6607.
Wrathall, J. R et al. (1997), Exp. Neurol. 145:565-573.
Xu, J et al. (2001), J. Neurotrauma 18, 523-532
Ye, Z. and Westlund, K. N. (1996), NeuroReport 7:2581-2585.
Yamagata K et al. (1993), Neuron., 11 (2):371-86.
Yang, K et al. (1995), Neurosci. Lett. 197(2): 101-104.
Yang, X et al. (1999), Bioorg. Med. Chem. Lett. 9, 3357-3362.
Yezierski, R. P et al. (2004), Neurosci. Lett. 361:232-236.
Yong, C et al. (1998), J. of Neurotrauma 15:459-472.
Yu, Z et. al. (1999) J. Neurosci. 19(20): 8856-8865.
Yune T Y et al. (2004) J. Neurotrauma 21:293-306.
Zabel, U and Baeuerle, P A. (1990). Cell. 61(2): 255-265.

---

What is claimed is:

1. A method for treating neuropathic pain in an individual, comprising:

administering a p65/p50 NF-κB oligonucleotide decoy having the nucleotide sequence as set forth in SEQ ID NO:6, wherein said administration of the oligonucleotide decoy ameliorates neuropathic pain in the individual.

2. The method of claim 1, wherein the neuropathic pain is due to spinal cord injury.

3. The method of claim 1, wherein the oligonucleotide decoy is at least 20 nucleotides and at most 50 nucleotides in length.

4. The method of claim 1, wherein the oligonucleotide decoy is 20 nucleotides in length.

5. A method for altering an inflammatory cascade in spinal cord injury, comprising:

administering a p65/p50 NF-κB oligonucleotide decoy having the nucleotide sequence as set forth in SEQ ID NO:6 to a subject having a spinal cord injury, wherein said administration ameliorates the inflammatory cascade at the NF-κB level by blocking p65/p50 binding.

6. The method of claim 5, wherein the oligonucleotide decoy is at least 20 nucleotides and at most 50 nucleotides in length.

7. The method of claim 5, wherein the oligonucleotide decoy is 20 nucleotides in length.

* * * * *